United States Patent [19]
Tailhan-Lomont et al.

[11] Patent Number: 5,973,009
[45] Date of Patent: Oct. 26, 1999

[54] AROMATIC DISELENIDES AND SELENOSULFIDES, THEIR PREPARATION AND THEIR USES, MORE PARTICULARLY THEIR THERAPEUTICAL USE

[75] Inventors: Catherine Tailhan-Lomont, Boissise le Roi; Irène Erdelmeier, Paris; Marc Moutet, Bagneux; Jean Chaudiere, Saint Maur des Fosses; Jean-Claude Yadan, Montreuil, all of France

[73] Assignee: Oxis International S.A., Portland, Oreg.

[21] Appl. No.: 08/997,669

[22] Filed: Dec. 23, 1997

[30] Foreign Application Priority Data

Dec. 27, 1996 [FR] France .................................. 96 16103

[51] Int. Cl.$^6$ .................................. A61K 31/095
[52] U.S. Cl. .................................. 514/706; 562/899
[58] Field of Search .................................. 562/899; 514/706, 514/422, 654

[56] References Cited

U.S. PATENT DOCUMENTS 5,128,365   7/1992   Spector et al. .................................. 514/422

OTHER PUBLICATIONS

Potapov et al, "Process for Producing Vinyl Phenyl Chalcogenides", Chem. Abs. 124:260560 of SU 1825363, 1996.

*Primary Examiner*—Deborah C. Lambkin
*Attorney, Agent, or Firm*—Klauber & Jackson

[57] ABSTRACT

The objects of the present invention are:
  novel organoselenium compounds: aromatic diselenides and selenosulphides;
  the use of said novel compounds as antioxidant agents;
  pharmaceutical compositions containing them;
  a method of preparation of said novel compounds. pa Said novel cyclic organoselenium compounds have the general formula (I):

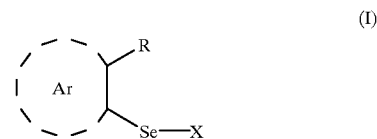

(I)

14 Claims, 3 Drawing Sheets

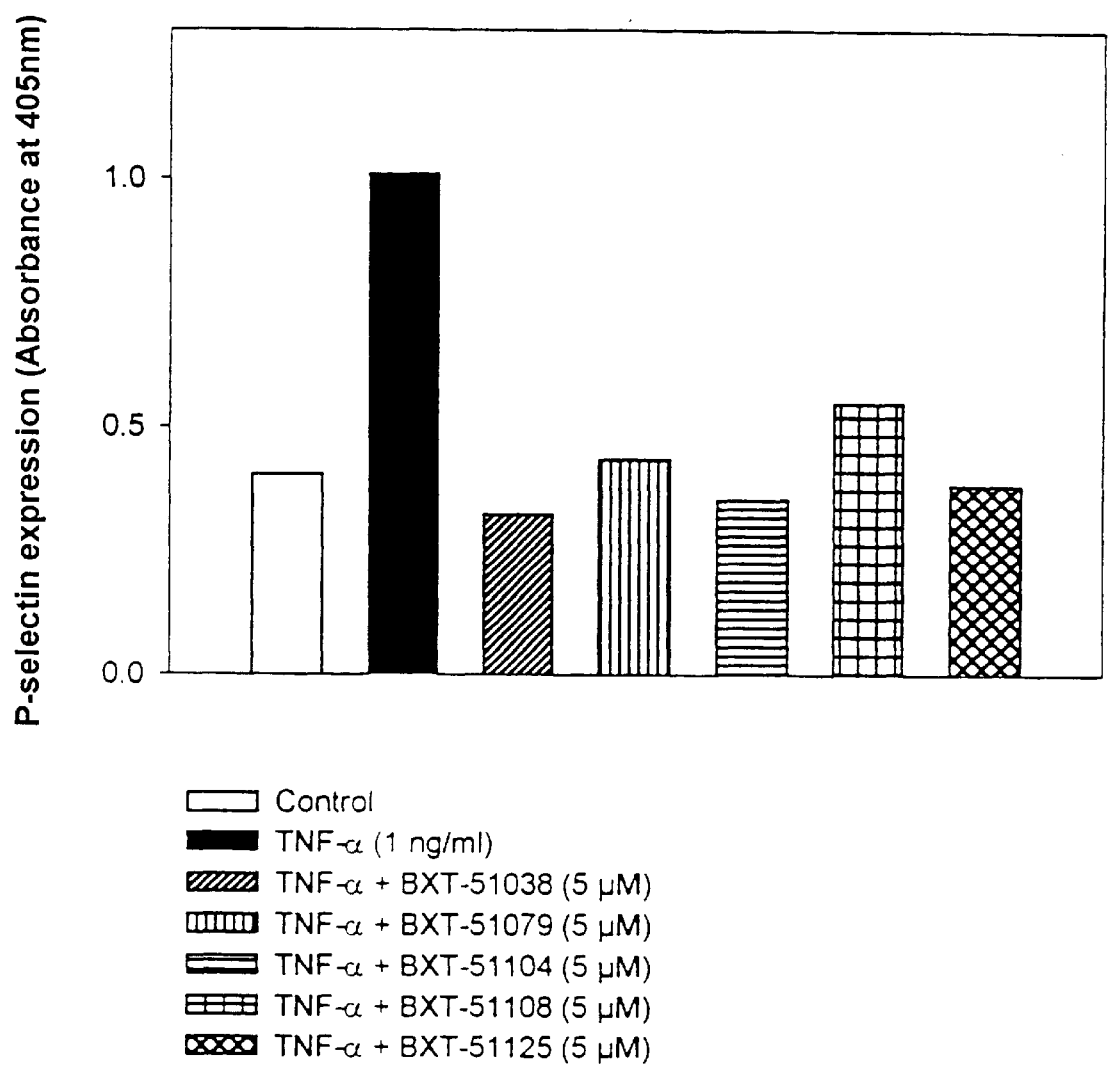

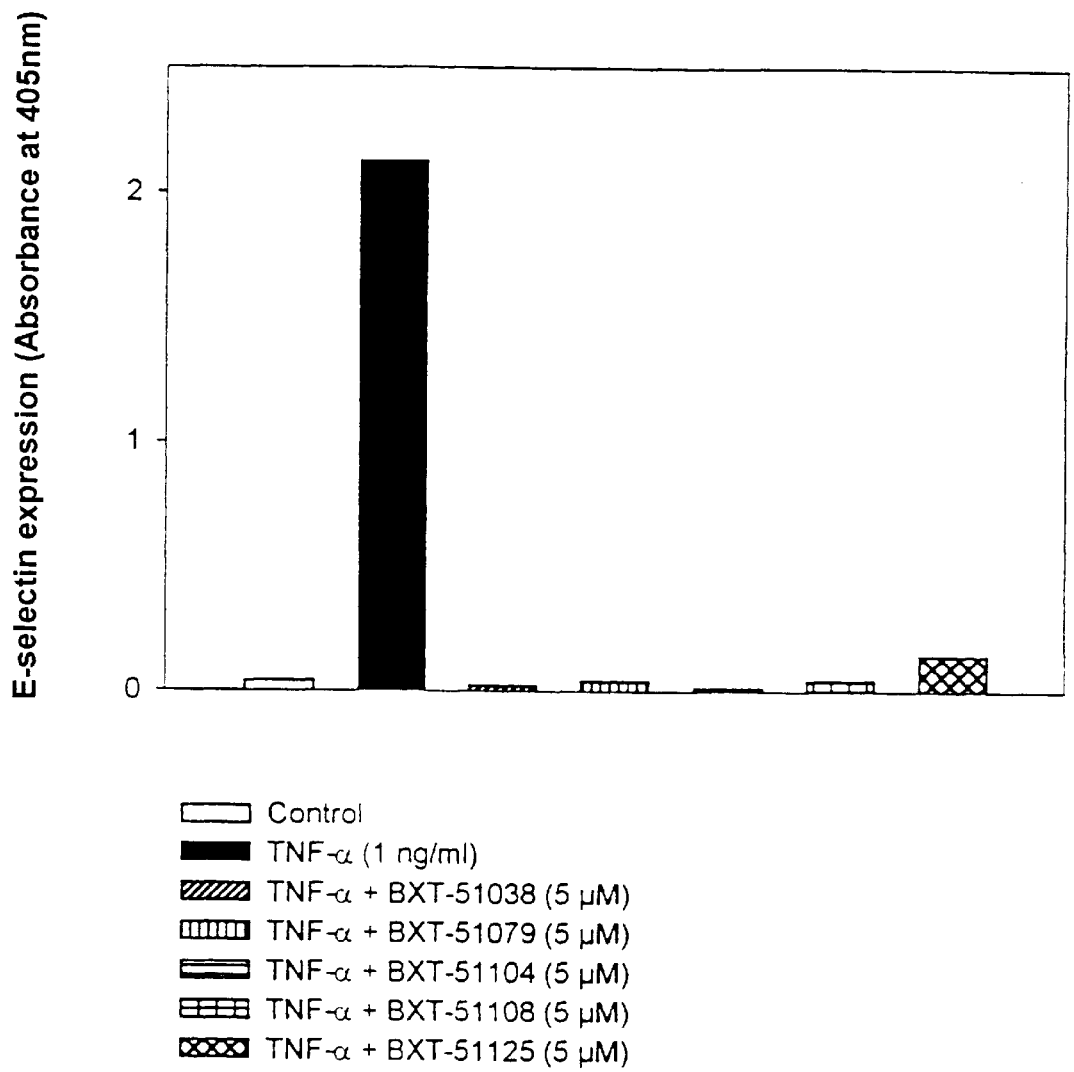

AROMATIC DISELENIDES AND SELENOSULFIDES, THEIR PREPARATION AND THEIR USES, MORE PARTICULARLY THEIR THERAPEUTICAL USE

The principal objects of the present invention are:
novel organoselenium compounds:aromatic diselenides and selenosulphides;
the use of said novel compounds as antioxidant;
pharmaceutical compositions containing them;
a method of preparation of said novel compounds.

STATE OF THE PRIOR ART

In aerobic organisms, during the metabolism of oxygen, very reactive entities are generated whose accumulation causes deleterious effects. These organisms possess a system of regulation, composed of enzymes and small molecules which enable controlling the production of these reactive oxygen entities. Amongst the various components of this regulation system, often called Antioxidant Defence System, glutathione peroxidases play a central role in the prevention of <<oxidative stress>> and its deleterious consequences. These antioxidant and cytoprotecting enzymes enable degrading the endogenous or exogenous cytotoxic hydroperoxides.

These enzymes catalyse the reduction of hydrogen peroxide (reaction 1) or that of organic hydroperoxides (reaction 2) by reduced glutathione (GSH):

reaction 1:

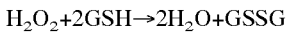
$H_2O_2 + 2GSH \rightarrow 2H_2O + GSSG$ reaction 2:

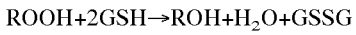
$ROOH + 2GSH \rightarrow ROH + H_2O + GSSG$

The active sites of these enzymes all contain one essential selenium atom in the form of a selenocysteine residue incorporated in the polypeptide chain.

The selenium is incorporated from selenite salts, or selenate salts, or L-seleno-methionine salts arising from food (see C. K. Chow and J. Jeng; in Selenium in Medicine and Biology, M. D. Spallholz and H. E. Ganther Eds.; (1986); Academic Press). In situations of selenium deficiency in the diet, the concentrations and activities of these glutathione peroxidases gradually decrease (see Y. X. Wang and J. Kiem.; Biological Trace Elements Res.; (1988); 15; 89 and see R. Reiter and A. Wendel; Biochem. Pharmacol.; (1983); 32; 3063–3067); this leads to an acute susceptibility to the oxidative stress (see D. B. Coursin and H. P. Cihla, Thorax, (1996), 51. 479–483). The provision of selenium in the diet is therefore a limiting factor in the biosynthesis of glutathione peroxidases.

The protecting role of glutathione peroxidases, in situations wherein the production of hydroperoxides rises, has been demonstrated following experiments of direct intracellular micro-injection of the enzyme of erythrocyte origin which have enabled demonstrating its cytoprotective effect upon the viability of fibroblasts or endothelial cells exposed to an oxidative stress (see C. Michiels et al.; Experiment. Cell Res.; (1988); 179; 581–589). On the other hand, it has been shown that the survival of human fibroblasts is appreciably lowered when glutathione peroxidase is inhibited (see C. Michiels et al., J. Eur. Biochem., 1988,177, 435–441).

Furthermore, the glutathione peroxidases are themselves particularly sensitive to an over-production of hydroperoxides and are rapidly inhibited under these conditions (see H. Ochi et al., Arch. of Biochem. Biophys., (1992), 294, 2, 407–411).

A certain number of pathologies such as certain ischaemic cardiomyopathies for example (see J. Chaudière, in Biologie des lipides chez l'Homme, L. Doustes-Blazy and F. Mendy eds, Edition Médicale Internationale—Paris, (1988), 137–154 and see D. Vitoux et al.; Ann. Biol. Clin.; (1996); 54; 5; 181–187) are associated with a lowering of glutathione peroxidase activity.

The demonstration of the essential role of the selenium at the active centre of these ubiquitous enzymes (see J. T. Rotruck, in Selenium in Biology and Medicine, Spallholz, J. E. Martin, J. L. Ganther H. I. eds., Avi Publishing Co, Wesport, (1981), 10–16) as well as the importance of the selenium in the regulation of oxidative damages generated during certain pathologies (see Cadenas, E. and Sies, H., Adv. Enz. Regul., (1985), 23, 217–237 and see Ursini, F., Bindoli, A., Chem. Phys. Lipids, (1987), 44, 255–276) has enabled the emergence of a novel class of organoselenium compounds as potential drugs.

Two types of compounds have been designed and prepared to this end.

On one side, modified macromolecules possessing a selenium atom introduced chemically such as selenosubtilisin (see Z. P. Wu and D. Hilvert, J. Am. Chem. Soc., (1990), 112, 5647–5648) or even a seleno-abzyme (see G. M. Luo et al., Biochem. Biophys. Res. Comm., 1994, 198, 3, 1240–1247). However, the use of proteins with a therapeutic aim is difficult to envisage for the following reasons:

their biostability is often insufficient;
an efficient method for ensuring their intra-cellular targeting does not exist;
they cannot be administered orally.

On the other side, synthetic molecules of low molecular weight have been synthetized, of which 2-phenyl-1,2-benzisoselenazolin-3-one (ebselen) (see H. Sies, Free Rad. Biol. Med., (1993), 14, 313–323) was the first compound described as having a glutathione peroxidase activity. Homologs of said ebselen, i.e. 2H-3,4-dihydro-1,2-benzoselenazin-3-ones, have also been described by Pierre V. Jacquemin et al. in Tetrahedron Letters, (1992), Vol. 33, No. 27, 3863–3866. In fact, several organoselenium derivatives have been described as glutathione peroxidase mimics, i. e. capable of reducing hydroperoxides in the presence of a biological thiol such as glutathione or lipoic acid (see I. A. Cotgreave et al., Biochem. Pharmacol., (1992), 43, 793–802 and C. M. Andersson et al., Free Rad. Biol. Med., (1994), 16, 17–28 and S. R. Wilson et al., J. Am. Chem. Soc., (1989), 111, 5936–5939 and V. Galet et al., J.Med.Chem., (1994), 37, 2903–2911). The patent application WO-A-95/27706 describes compounds of benzisoselenazoline and benzisoselenazine structure having a glutathione peroxidase activity inter alia. U.S. Pat. Nos. 5,128,365 and 5,321,138 themselves describe organic diselenides having glutathione peroxidase activity.

These organoselenium compounds, which are mimics of glutathione peroxidase, invariably produce catalytic intermediates of the selenol and/or diselenide type.

Amongst these, 2-phenyl-1,2-benzisoselenazolin-3-one (ebselen) and some of its derivatives do not seem to have any major toxic effect (see A. Wendel et al.; Biochem. Pharmacol.; (1984); 33; 3241–3245 and S. D. Mercurio and G. F.

Combs; Biochem. Pharmacol.; (1986); 35; 4505–4509).
2-Phenyl-1,2-benzisoselenazolin-3-one (ebselen) is however very little soluble in water, even in the presence of an excess of glutathione GSH, which limits its pharmacological applications.

The biochemical and pharmacological properties of the organoselenium compounds which have been synthesised and studied have been recently reviewed ( see M. J. Parnham and E. Graf; Progress in Drug Res.; (1991); 36; 9–47 and M. J. Pamham, Exp. Opin. Invest. Drugs, (1996), 5, 7, 861–570).

One of the aims of the present invention is to design organoselenium compounds having a catalytic activity of the glutathione peroxidase type in the presence of physiological concentrations of glutathione GSH.

These compounds must be able to penetrate the target tissues or cells, be soluble in water at active concentrations and must not efficiently reduce oxygen into toxic by-products.

These aims are attained by virtue of the present invention which resides on the design of cyclic organoselenium compounds whose antioxidant and cytoprotecting activities have been demonstrated by the Applicant and which are given below.

From a chemical point of view, very few 4(5)-seleno-imidazole derivatives have been described in the literature. Generally, these 4(5)-seleno-imidazole derivatives have been accessed according to 2 main routes, namely:

either by reaction between a derivative of type N-(trialkylsilyl)-imidazole and an arylselenium halide (see T. G. BACK and R. G. KERR; Can. J. Chem.; (1986); 64; 2; pages 308–301);

or by nucleophilic substitution between a 4-halo-imidazole derivative and a selenium derivative such as selenourea (see G. H. MILNE and L. R. TOWNSEND; J. Carbohydr. Nucleosides, Nucleotides; (1976); 3; 3; pages 177–183) or sodium hydrogen selenide (see G. H. MILNE and L. R. TOWNSEND; J. Heterocycl. Chem.; (1976); 13; 4; pages 745–748);

One of the objects of the invention described in this patent is to propose a novel method of introducing selenium in position 4(5) of an imidazole ring by reaction with an electrophilic selenium derivative such as selenium ($Se^I$) chloride.

DESCRIPTION OF THE INVENTION

The aim of the present invention is:
1) to solve the novel technical problem consisting of providing novel aromatic diselenides and selenosulphides having a very good antioxidant and cytoprotecting activity, thus constituting valuable active principles of pharmaceutical compositions;
2) to solve the novel technical problem above according to a solution which includes a method of preparation of these novel compounds which is easy to carry out.

The technical problems set forth above are solved for the first time in a simultaneous manner by the present invention in a simple way; the method of preparation of said novel compounds being relatively easy to carry out and giving good yields.

According to its first aspect, the present invention thus relates to novel organoselenium compounds—aromatic diselenides and selenosulphides—having the general formula (1) below:

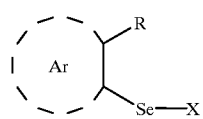

(I)

in which:

R=hydrogen; —C($R_1R_2$)—A—B;

$R_1$=lower alkyl; optionally substituted aryl; optionally substituted lower aralkyl;

$R_2$=lower alkyl: optionally substituted aryl: optionally substituted lower aralkyl;

A=CO; $(CR_3R_4)_n$;

B represents $NR_5R_6$; $N+R_5R_6R_7Y^{13}$; $OR_5$; $SR_5$;

Ar=an optionally substituted phenyl group or an optionally substituted radical of

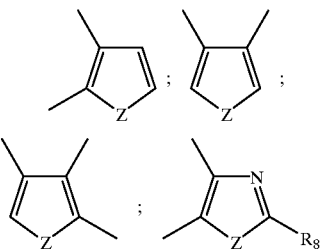

in which Z represents O; S; $NR_5$; when R=—C($R_1R_2$)—A—B or

Ar=a radical of formula

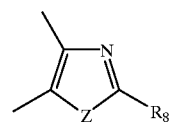

in which Z=O; S; $NR_5$; when R is hydrogen;

X = Ar(R)—Se—; —S-glutathione; —S—N-acetylcysteine; —S-cysteine; —S-penicillamine; —S-albumin; —S-glucose;

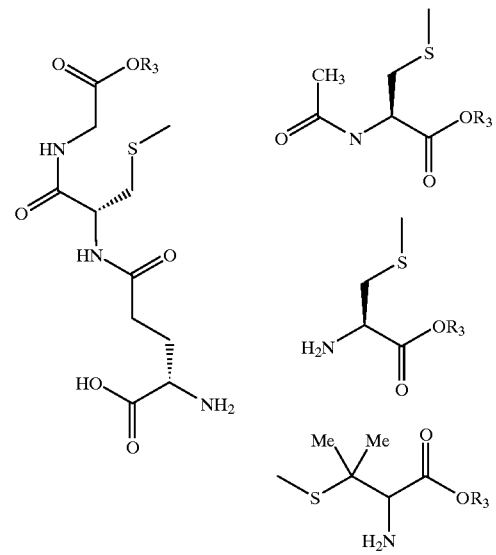

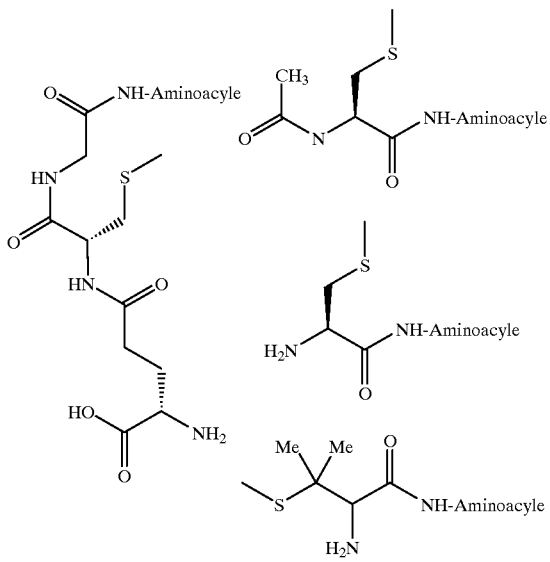

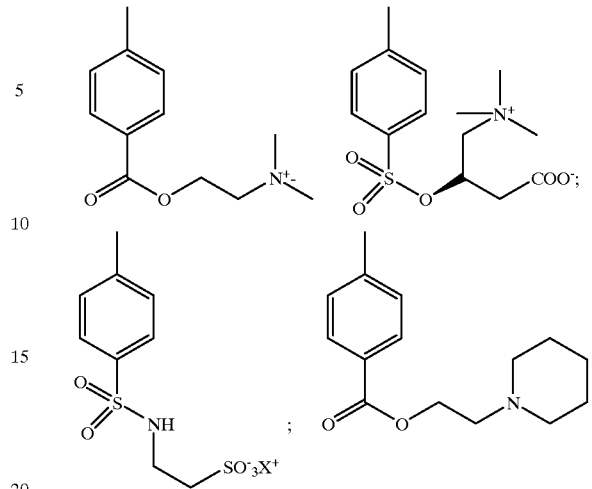

R$_3$32 hydrogen; lower alkyl; optionally substituted aryl, optionally substituted lower aralkyl;

R$_4$32 hydrogen; lower alkyl; optionally substituted aryl: optionally substituted lower aralkyl;

R$_5$=hydrogen; lower alkyl; optionally substituted aryl: optionally substituted lower aralkyl; optionally substituted heteroaryl; optionally substituted lower heteroaralkyl; CO(lower alkyl); CO(aryl); SO$_2$ (lower alkyl); SO$_2$(aryl);

R$_6$32 hydrogen; lower alkyl; optionally substituted aryl; optionally substituted lower aralkyl; optionally substituted heteroaryl; optionally substituted lower heteroaralkyl;

R$_7$32 hydrogen; lower alkyl; optionally substituted aryl: optionally substituted lower aralkyl; optionally substituted heteroaryl; optionally substituted lower heteroaralkyl;

R$_8$32 hydrogen; lower alkyl; optionally substituted aryl; optionally substituted lower aralkyl; optionally substituted heteroaryl; optionally substituted lower heteroaralkyl; trifluoromethyl;

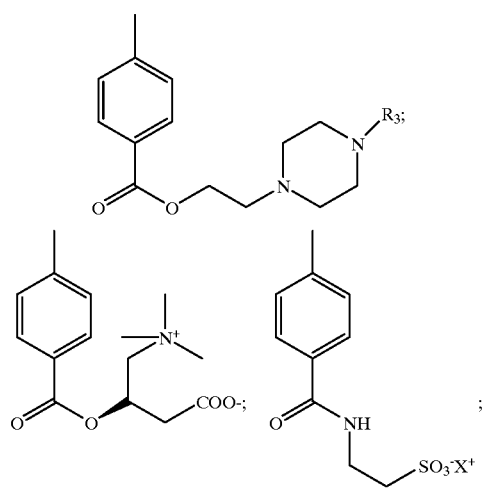

n=0 or 1;

X$^+$represents the cation of a pharmaceutically acceptable base;

Y$^-$represents the anion of a pharmaceutically acceptable acid;

and their salts of pharmaceutically acceptable acids or bases;

with the provisos that:
when R=—C(R$_1$R$_2$)—(CR$_3$R$_4$)—B with B=NR$_5$R$_6$ or N$^+$R$_5$R$_6$R$_7$Y$^-$ and
X=Ar(R)—Se— with Ar=optionally substituted phenyl,
then —C(R$_1$R$_2$) is different from (CR$_3$R$_4$); and
when Ar=phenyl and
R=—C(R$_1$R$_2$)—C(O)—B with B=NH$_2$ or NHCH$_3$ or NHCH$_2$C$_6$H$_5$ or NHC$_6$H$_5$ and
X=Ar(R)—Se—,
then R$_1$ and R$_2$ cannot simultaneously represent a methyl group.

Said general formula (I) includes every stereoisomer, epimer and diastereoisomer, as a mixture or in isolated form.

It also includes, as indicated, the salts of pharmaceutically acceptable acids or bases of said compounds of formula (I).

Amongst the pharmaceutically acceptable acids, hydrochloric, hydrobromic, hydroiodic, sulphuric, tartaric, methanesulphonic, trifluoromethanesulphonic acid, . . . can be cited in a non-limiting way.

Amongst the pharmaceutically acceptable bases, sodium hydroxide, potassium hydroxide, alkali metal or alkaline earth metal carbonates, or organic bases such as triethylamine or arginine, . . . can be cited in a non-limiting way.

Within the context of the present description and annexed claims:
the terms "lower alkyl and lower alkoxy (see below)" are understood as meaning straight or branched alkyl and alkoxy groups having from 1 to 8 carbon atoms;
the term "aryl" is understood as meaning an aromatic group selected from phenyl and naphthyl groups;
the term "heteroaryl" is understood as meaning a mono- or bicyclic aromatic group, each cycle, or ring, comprising five or six atoms and said cycle, or ring, or both cycles, or rings, including in its carbon skeleton from one to three heteroatoms selected from nitrogen, oxygen and sulphur;

the terms "lower aralkyl" and "lower heteroaralkyl" are understood as meaning, in view of the definitions above, phenyl($C_1$–$C_8$)alkyl or naphthyl($C_1$–$C_8$)alkyl and heteroar($C_1$–$C_8$)alkyl respectively;

the term "substituted" concerning the terms aryl, aralkyl, phenyl, radical (five-membered, including Z), heteroaryl, heteroaralkyl, as defined above, signifies that the groups in question are substituted on the aromatic part with one or more identical or different groups selected from the groups: ($C_1$–$C_8$)alkyl, trifluoromethyl, ($C_1$–$C_8$)alkoxy, hydroxy, nitro, amino, ($C_1$–$C_8$)alkylamino, di($C_1$–$C_8$)alkylamino, sulphoxyl, sulphonyl, sulphonamide, sulpho($C_1$–$C_8$)alkyl, carboxyl, carbalkoxyl, carbamide (it being possible for said ($C_1$–$C_8$)alkyl groups to be linear or branched) or substituted with one or more halogen atoms;

the term aminoacyl, which concerns the glutathionyl, cysteinyl, N-acetylcysteinyl or even the penicillaminyl group in the definition of X, signifies any natural aminoacid such as alanine, and leucine, . . . for example.

when $R_5$ and/or $R_6$ represents a hydrogen atom, the invention also covers the salts obtained with the pharmaceutically acceptable acids.

Said novel compounds have proved to be, as specified above, excellent antioxidant agents, the use of which is recommended by the Applicant in various fields. This use of said novel cyclic organoselenium compounds of the invention—compounds having formula (I) as defined above—as antioxidant agents, constitutes the second aspect of said invention.

Within the context of this second aspect, the use of said compounds of formula (I), is more particularly claimed as antioxidant:

intended to be added to preserving media of grafts for transplantation of organs of human or animal origin such as the heart, the liver, the kidney and the lungs; and intended for (as active principle) the manufacture of pharmaceutical compositions with antioxidant activity, suitable especially:

for treatments of any physiopathological condition in which an over-production of cytotoxic hydroperoxides contributes to the functional impairments of cells or tissues; and more particularly including:

the treatment of inflammatory and/or ischaemic cardio- and cerebro-vascular pathologies, such as the preventive and/or curative treatment of arterial restenoses following an angioplasty, the preventive and/or curative treatment of arterial stenoses following artery allografts, the treatment of intermittent claudication in patients affected with obstructive ischaemia of the lower members, the treatment of cerebro-vascular accidents of ischaemic origin;

the treatment of inflammatory and/or ischaemic digestive pathologies, such as the treatment of acute inflammations of the bowel (Crohn's disease, hemorrhagic rectocolitis);

the treatment of inflammatory and/or ischaemic respiratory pathologies, such as the treatment of adult respiratory distress syndrome (ARDS) and infant respiratory distress syndrome (IRDS);

the treatment of inflammatory and/or ischaemic ophthalmic pathologies, such as the treatment of glaucoma;

the treatment of cataracts;

the treatment of acute ophthalmic allergies;

the treatment of impairments of the retina which are associated with a macular degeneration;

the treatment of viral infections causing an immunodeficiency, such as the treatment of AIDS;

the treatment of post-radiotherapy fibroses.

Generally, the potential therapeutic applications of the compounds of the invention include the treatment of any physiopathological condition in which an over-production of cytotoxic hydroperoxides contributes to the functional impairments of cells or tissues. Such an over-production of hydroperoxides can be endogenous and secondary to the activation of the intra-cellular metabolic pathways such as, for example, those of the flavine or cytochrome P-450 oxygenases, those of the lipoxygenases, those of the monoamine oxidases. The over-production can also be due to the activation of the endothelial cells (xanthine oxidase, 15-lipoxygenase), or of blood platelets (cyclooxygenase and 12-lipoxygenase). It can also be due to the activation, by cytokines such as TNF-α for example, of inflammatory and/or immune cells such as neutrophils, macrophages or lymphocytes for example. It may also be due to an intoxication by a free-radical generating xenobiotic. Finally, it may be due to a voluntary irradiation such as practised during a radiotherapy, or an accidental irradiation.

More particularly, the second aspect of the present invention includes the use of compounds of the invention for the manufacture of pharmaceutical compositions intended for the treatment:

of inflammatory diseases of the bowel such as Crohn's disease or hemorrhagic rectocolitis;

of adult respiratory distress syndrome and infant respiratory distress syndrome;

of cataracts;

of AIDS;

of post-radiotherapy fibroses.

From the second aspect of the present invention—use of the novel compounds de formula (I) as antioxidant agents—, such as described now, comes the third aspect which is dealt with now, namely the pharmaceutical compositions containing said compounds of formula (I) as active principle.

Thus, according to its third aspect, the present invention relates to pharmaceutical compositions, notably having an antioxidant activity, and comprising at least one organoselenium compound of the general formula (I), or one of its pharmaceutically acceptable salts of an acid or a base, as active ingredient, optionally incorporated in a pharmaceutically acceptable excipient, carrier or vehicle.

Said pharmaceutical compositions of the invention, according to an advantageous embodiment, contain said active ingredient in an amount between 0.1 and 5% by weight, advantageously between 0.1 and 1% by weight based on their total weight. According to another advantageous embodiment, said compositions are in the form of unit doses comprising from 1 to 500 mg of at least one cyclic organoselenium compound of the invention (optionally incorporated in a pharmaceutically acceptable excipient, carrier or vehicle).

The pharmaceutical compositions of the invention can be formulated for, or intended for, oral, rectal or topical administration, (the compounds of formula (I) may especially be formulated for ophthalmic applications in the form of an eye lotion) or even as intra-ventricular, intramuscular, subcutaneous or intravenous injections.

The pharmaceutically acceptable excipients, vehicles and carriers which can be included in their formulation are products which are well-known to the person skilled in the art and are not described in detail here.

The pharmaceutical compositions of the invention which contain the antioxidant agents disclosed by the present invention (compounds of formula (I)) are especially suitable for the treatment of any physiopathological condition in which an over-production of cytotoxic hydroperoxides contributes to the functional impairments of cells or tissues; it being possible for said over-production of hydroperoxides to be due to any one of the causes presented above in the present description, with reference to the second aspect of the invention (activation of the intra-cellular metabolic pathways, enzyme activation, macrophage or lymphocyte activation, intoxication by a free-radical generating xenobiotic, voluntary or accidental irradiation).

More specifically, said pharmaceutical compositions are suitable for the treatment of the pathologies listed above in the present description (with reference to the second aspect of the invention).

It is hereby specified that the antioxidant and therapeutical or pharmacological activities of the cyclic organoselenium compounds of the general formula (I) above have been demonstrated according to safe and reliable tests well-known to the person skilled in the art, which comprise:

a/ measuring the glutathione peroxidase activity;

b/ measuring the cytoprotective effect in human umbilical vein endothelial cells.

It is hereby incidentally mentioned that the preparation of pharmaceutical compositions incorporating an effective amount of at least one organoselenium compound of formula (I) according to the invention as well as the therapeutical treatments implying the use of such a compound make up an integral part of the present invention.

According to its last aspect, given below, the invention even relates to a method of preparation of said organoselenium compounds of formula (I). In fact, two synthetic routes are recommended:

a route B for the compounds of formula (I) in which R=H;

a route A for the other compounds of formula (I) in which R≠H; R=—C($R_1R_2$)—A—B.

First of all, said route A is presented. It comprises the following essential steps:

a/ preparing or using an orthohalo(hetero)arylacetonitrile derivative, optionally mono-or gem- disubstituted in the benzylic position; then, according to the series considered:

for the preparation of said compounds of formula (I) in which A=$(CR_3R_4)_n$ and n=0 (A does not exist):

b1/ hydrolyzing said nitrile derivative into an amide derivative, c1-1/ transforming this amide derivative into an amine derivative by a transposition reaction according to conventional methods, d1-1/ allowing said amine derivative to react with a nucleophilic selenium derivative, optionally generated in situ, in the presence of a copper Cu(I) salt, in a polar organic solvent, to lead to the corresponding (hetero)arylisoselenazoline derivative, e1-1/ optionally, N-alkylating or N-arylating or N-acylating or N-sulphonylating, according to conventional procedures, said (hetero) arylisoselenazoline derivative;

for the preparation of said compounds of formula (I) in which A=CO:

b1/ hydrolyzing said nitrile derivative into an amide derivative, c1-2/ allowing said amide derivative to react with a nucleophilic selenium derivative, optionally generated in situ, in the presence of a copper Cu(I) salt, in a polar organic solvent, to lead to the corresponding (hetero)arylisoselenazone derivative, d1-2/ optionally, N-alkylating or N-arylating or N-acylating or N-sulphonylating, said (hetero) arylisoselenazone derivative;

for the preparation of said compounds of formula (I) in which A=$CH_2$:

b2/ reducing said nitrile derivative into an amine derivative with the aid of borane for example in an ethereal solvent such as tetrahydrofuran for example, c2/ allowing said amine derivative to react with a nucleophilic selenium derivative, optionally generated in situ, in the presence of a copper Cu(I) salt, in a polar organic solvent, to lead to the corresponding (hetero)arylisoselenazine derivative, d2/ optionally, N-alkylating or N-arylating or N-acylating or N-sulphonylating, according to conventional procedures, said (hetero) arylisoselenazine derivative;

for the preparation of said compounds of formula (I) in which A=($CR_3R_4$) (≠$CH_2$):

b3/ carrying out a mono- or a bis-C-alkylation of said nitrile derivative according to conventional methods, with the aid of an organolithium derivative for example, in an ethereal solvent such as tetrahydrofuran;

c3/ allowing the amine derivative obtained to react with a nucleophilic selenium derivative, optionally generated in situ, in the presence of a copper Cu(I) salt, in a polar organic solvent, to lead to the corresponding (hetero)arylisoselenazine derivative;

d3/ optionally, N-alkylating or N-arylating or N-acylating or N-sulphonylating, according to conventional procedures, said corresponding (hetero)arylisoselenazine derivative;

b/ reducing, in a polar solvent such as methanol, the cyclic compound obtained, according to any one of the above synthetic routes, with the aid of a metal hydride, such as sodium borohydride, intervening in an amount corresponding to a half-reducing equivalent; for the preparation of said compounds of formula (I) in which X=Ar(R)—Se—; or allowing said cyclic compound obtained according to any one of the above synthetic routes to react at ambient temperature, with the thiol compound corresponding to the values of X≠Ar(R)—Se—, for the preparation of said compounds of formula (I) in which X≠Ar(R)—Se—.

Said method is close to that described in the application WO-A-95/27706. It consists, as appears clearly above, of two main steps:

upon completion of the first (a/), cyclic organoselenium compounds are obtained;

during the second (b/), said cyclic organoselenium compounds are either reduced or allowed to react with a thiol.

The implementation of each of its steps does not give rise to any particular difficulty to the person skilled in the art.

According to the advantageous variants of implementation of said method:

the nucleophilic selenium derivative (which intervenes in steps d1-1/, c1-2/, c2/ and c3/) is a selenocyanate salt, such as potassium selenocyanate for example, which can be:

either generated in situ from selenium metal Se(0) and a cyanide salt, such as potassium cyanide for example, or added to the reaction medium as such;

the copper salt Cu(I) (which intervenes in the same steps) is cuprous iodide;

the polar organic salt (which intervenes in the same steps) is dimethylformamide.

Route B is now presented. This is an original method of preparation, notably of 4(5)-seleno-imidazole derivatives of formula (I), more specifically compounds of the invention of formula (II) below:

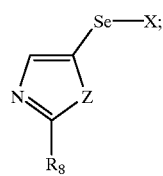

(II)

in which Z and $R_8$ (and X) are defined as above with reference to the general formula (I).

Said original method comprises the following essential steps:

a/ preparing or using a derivative of formula (III):

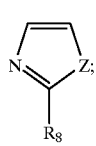

(III)

N-alkylated, N-arylated, N-acylated or N-sulphonylated when $Z=NR_5$; then, according to the series considered:

for the preparation of said diselenide compounds of formula (II) in which $R_8$32 hydrogen:
  b1/ allowing said derivative of formula (III) to react with an electrophilic selenium derivative, in a non-polar solvent;
  c1/ if necessary, de-acylating or de-sulphonylating, according to usual procedures, the compound obtained;

for the preparation of said diselenide compounds of formula (II) in which $R_8$32 lower alkyl, optionally substituted lower aralkyl, optionally substituted lower heteroaralkyl:
  b2/ alkylating said derivative of formula (III) in position 2 in treating it firstly with an organolithium base such as lithium diisopropylamide, then, with a halide, notably a lower alkyl, optionally substituted lower aralkyl or optionally substituted lower heteroaralkyl iodide;
  c2/ allowing said alkyl derivative to react with an electrophilic selenium derivative, in a non-polar solvent;
  d2/ if necessary, de-acylating or de-sulphonylating, according to usual procedures, the compound obtained;

for the preparation of said diselenide compounds of formula (II) in which $R_8$32 optionally substituted aryl, optionally substituted heteroaryl:
  b3/ treating said derivative of formula (III), in a non-polar organic solvent, in the presence of a strong base, with a trialkyltin halide or a zinc halide in order to obtain the corresponding stannyl or zinc derivative then treating said stannyl or zinc derivative with a haloaromatic derivative, in the presence of palladium, in a non-polar organic solvent;
  c3/ allowing the compound obtained to react with an electrophilic selenium derivative, in a non-polar solvent;
  d3/ if necessary, de-acylating or de-sulphonylating, according to usual procedures, the compound obtained;

b/ if necessary, allowing said diselenide compound obtained according to any one of the above synthetic routes, in a polar solvent, with an adequate mercaptan; in order to obtain the corresponding selenosulphide compound.

For the preparation of the compounds—diselenides and selenosulphides—of the invention of formula (I) in which R=H, the diselenides are generally prepared as indicated above which are optionally transformed into selenosulphides (see B set forth above).

The alkyl group of the imidazole derivatives ($Z=NR_5$) N-alkylated is advantageously an alkyl group having from 1 to 6 carbon atoms, notably a methyl group.

The acyl group of the imidazole derivatives ($Z=NR_5$) N-acylated is advantageously a pivaloyl or a benzoyl group.

The sulphonyl group of the imidazole derivatives (Z=NR5) N-sulphonylated is advantageously a tosyl group or a N,N-dimethylsulphonamide group.

According to an embodiment of this method (preparation variant for the diselenide compounds of formula (II) in which $R_8$ includes an aryl group: step b3/), this is characterised in that the trialkyltin halide is preferably tributyltin chloride or trimethyltin chloride. According to another embodiment of this method (same variant), this is characterised in that the zinc halide is preferably zinc chloride.

According to another particular embodiment of this method (same variant, same step b3/), this is characterised in that the above-mentioned strong base can be an alkyllithium, such as butyllithium for example, or a lithium amide, such as lithium diisopropylamide for example.

According to another embodiment of this method (same variant, same step b3/), this is characterised in that the non-polar organic solvent is preferably an ethereal solvent such as tetrahydrofuran for example.

According to yet another particular embodiment of this method (same variant, same step b3/), this is characterised in that the above-mentioned haloaromatic derivative is a chloro- or bromo- or iodo-aromatic derivative such as, for example, bromobenzene or 4-chloropyridine.

According to still another particular embodiment of this method (all variants), this is characterised in that the above-mentioned electrophilic selenium derivative can be selenium ($Se^I$) chloride.

According to still another particular variant of this method, this (all variants) is characterised in that the above-mentioned non-polar solvent can be dichloromethane for example.

When $Z=NR_5$, the protected nitrogen is deprotected, when necessary in a conventional way in a polar solvent. Said polar solvent can be tetrahydrofuran or acetonitrile, for example.

Finally, the polar solvent intervening in step b/ is advantageously acetonitrile.

Other aims, characteristics and advantages of the invention will appear clearly in the light of the following explanatory description made with reference to various non-limiting Examples given solely as illustration and which in no way limit the scope of the invention. In the Examples, all percentages are given by weight unless otherwise indicated.

In the annexed figures,

FIG. 2 shows the inhibition of the TNF-α-induced P-selectin expression by endothelial cells (HUVEC);

FIG. 3 shows the inhibition of the TNF-α-induced E-selectin expression by endothelial cells (HUVEC).

EXPERIMENTAL SECTION

Figure 1:
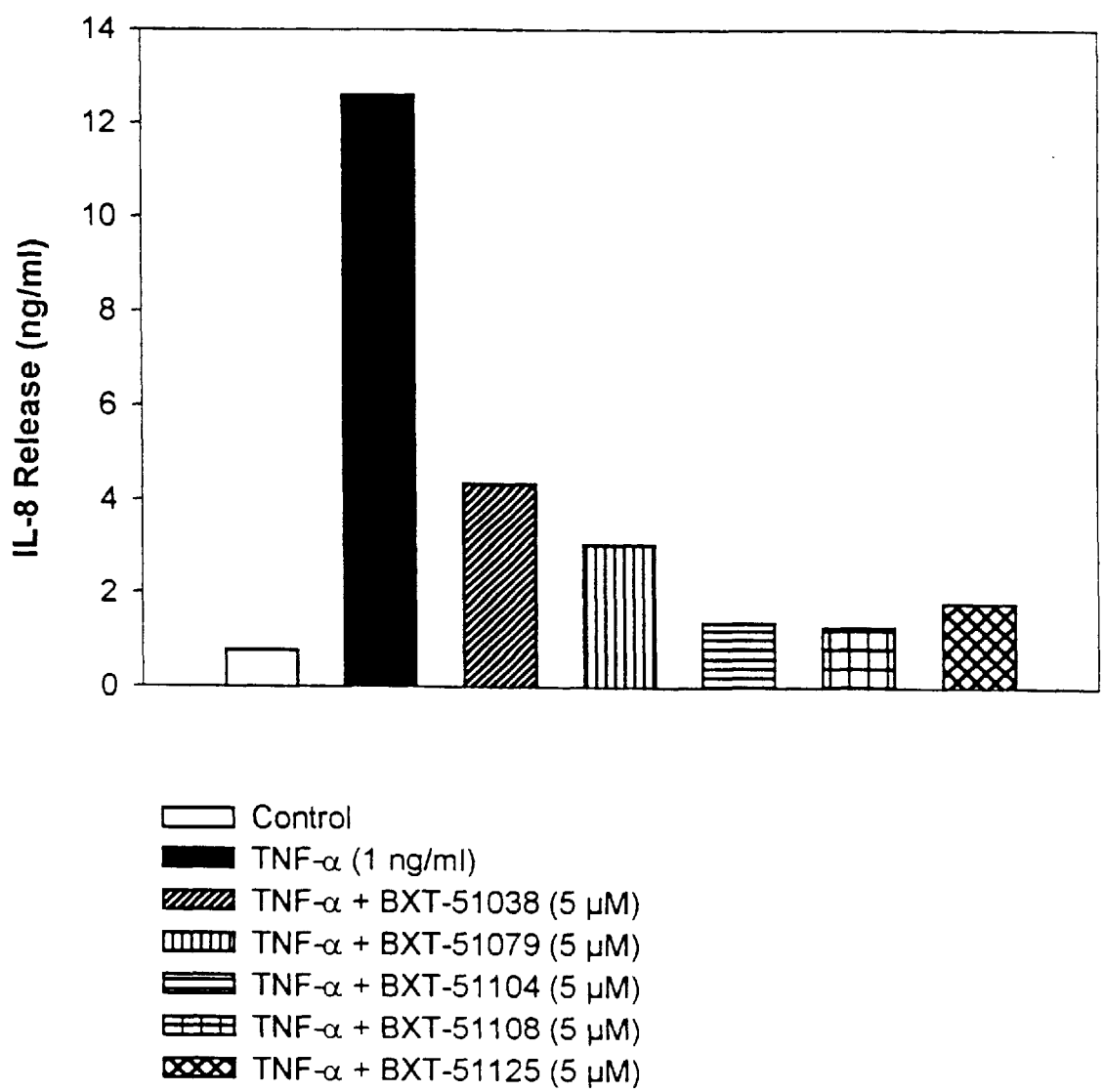
FIG. 1 shows the inhibition of the TNF-α-induced interleukin 8 release by endothelial cells (HUVEC)

All reactions were carried out under an inert nitrogen atmosphere unless otherwise indicated.

Mass spectra were recorded on a Nermag R10-10B instrument. Ionisation used is either electron impact (EI) at 70 electron-volts or chemical ionisation (CI) in ammonia or isobutene, or fast atom bombardment (FAB) on a glycerol matrix.

The $^1$H and $^{13}$C NMR spectra were recorded on a Varian Gemini-200 instrument, the $^{77}$Se NMR spectra on a Bruker AMX 500 instrument. The chemical shifts are given in ppm with respect to tetramethylsilane ($^1$H and $^{13}$C NMR spectra) or to dimethylselenide ($^{77}$Se NMR spectra). The multiplicities are expressed as follows: "s" for singlet, "bs" for broad singlet, "d" for doublet, "t" for triplet, "q" for quadruplet and "m" for multiplet; "E" for even and "O" for odd.

The melting points (m.p. ° C.) were recorded on a Gallenkamp instrument and are given uncorrected.

Purification by liquid column chromatography was carried out, according to the case, with Merck® Si60 $F_{254}$ or basic aluminium oxide Merck$^R$ $Al_2O_3$ 90 (Activity I).

I/ EXAMPLES OF SYNTHESIS OF COMPOUNDS OF GENERAL FORMULA I (≠II)

Example 1

Preparation of di[2-[2'-(1'-amino-2'-methyl)propyl]phenyl]-diselenide

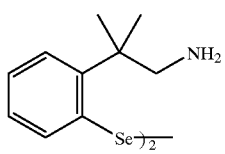

The 4,4-dimethylbenzisoselenazine derivative BXT 51072 (5.65 g; 25 mmoles) is suspended in anhydrous methanol (10 ml). A preparation of this derivative has been described in Example 8 of the application WO-A-95/27706.

Sodium borohydride (260 mg; 6.84 mmoles) is added slowly to the reaction medium, at a temperature of 0° C.; stirring is then continued for one hour at ambient temperature and under air. Tert-butyl methyl ether (40 ml) and a 50% saturated sodium chloride solution (10 ml) are added to the reaction medium, the latter is then decanted. The orange organic phase is washed with 10 ml of a 50% saturated sodium chloride solution, dried over magnesium sulphate and filtered.

The solvent is evaporated under reduced pressure. The desired product is obtained as an orange oil.

(Beware: the product dissolved in organic solvents, such as, for example dichloromethane, slowly oxidises in air to give the starting material, BXT 51072.)

Yield: 95%

Physical characteristics:

NMR $^1$H: (CDCl$_3$); 1.41 ppm (s; 6H); 1.60 ppm (bs; 2H); 3.08 ppm (s; 2H); 7.00–7.35 ppm (m; 3H); 7.95 ppm (m; 1H).

This product contains 6% of BXT 51072 according to the comparative integration of the small supplementary signals at 1.26 ppm and 3.21 ppm.

NMR $^{13}$C: (CDCl$_3$); 27.82 ppm; 42.65 ppm; 52.21 ppm; 127.98 ppm; 128.22 ppm; 128.97 ppm; 130.47 ppm; 136.45 ppm; 146.87 ppm.

NMR $^{77}$Se: (CH$_3$SeCH$_3$); 493 ppm

MS: (CI, isobutane); 457 (MH$^+$; 55%); 228 (100%).

HRMS: calc. for C20H29N2Se2: 457.0661; exp.: 457.0665.

Example 2

Preparation of di[2-[2'-(1'-amino-2'-methyl)propyl]phenyl]-diselenide dihydrochloride: BXT 51125

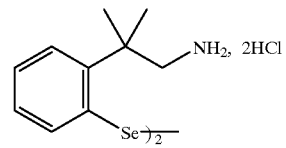

The 4,4-dimethylbenzisoselenazine derivative BXT 51072 (27.12 g; 0.12 mol) (see Example 8 of WO-A-95/27706) is suspended in anhydrous methanol (50 ml). Sodium borohydride (1.25 g; 33 mmoles) is added in portions of 50 mg for 30 min. to the reaction medium at a temperature of 0° C.; stirring is then continued vigorously for 5 hours at ambient temperature and under air. Tert-butyl methyl ether (200 ml) and a 50% saturated sodium chloride solution (50 ml) are added to the reaction medium, the latter is then decanted. The orange organic phase is washed with 50 ml of a 50% saturated sodium chloride solution, dried over magnesium sulphate and filtered. This solution is added slowly (50 min.) to an ethanolic solution of hydrogen chloride (68 ml; 4.1M; 0.28 mol) at a temperature of 5° C. Stirring is continued vigorously for 30 min. The suspension obtained is filtered. The yellow precipitate is washed with 5×50 ml of tert-butyl methyl ether, then dried. The desired compound is obtained as a yellow powder.

Yield: 95%

Physical characteristics:

m.p.° C.: 283° C. (dec.);

NMR $^1$H: (D$_2$O); 1.39 ppm (s; 6H); 3.42 ppm (s; 2H); 7.06 ppm (m; 1H); 7.25 ppm (m; 1H); 7.36 ppm (m; 1H); 7.65 ppm (m; 1H).

NMR $^1$H: (CD$_3$OD); 1.56 ppm (s; 6H); 3.52 ppm (s; 2H); 7.21 ppm (td; 1H, J=8-8-1.5 Hz); 7.36 ppm (td; 1H, J=8-8-1.5 Hz); 7.41 ppm (dd; 1H, J=8 −1.5 Hz); 7.80 ppm (dd; 1H, J=8-1.5 Hz).

NMR $^{13}$C: (D$_2$O); 24.95 ppm; 37.35 ppm; 46.29 ppm; 127.13 ppm; 127.27 ppm; 127.74 ppm; 127.90 ppm; 136.33 ppm; 142.07 ppm.

microanalysis: calc. for C20H30Cl2N2Se2: C 45.56%; H 5.73%; N 5.31%; exp. C 45.50%; H 5.77%; N 5.44%.

Example 3

Preparation of di[2-[2'-(1'-ammonium-2'-methyl) propyl]phenyl]-diselenide di-paratoluenesulphonate: BXT 51108

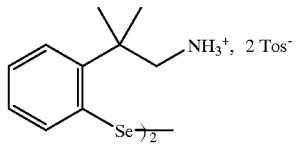

The 4,4-dimethylbenziseoselenazine derivative BXT 51072 (3.39 g; 15 mmoles) (see Example 8 of WO-A-95/27706) is dissolved in anhydrous methanol (75 ml). Sodium borohydride (627 mg; 16.5 mmoles) is added; then the reaction mixture is stirred for 30 min; at ambient temperature and under air. The methanol is evaporated under reduced pressure. The residue is taken up into 150 ml of ethyl acetate and washed with 2×50 ml of water; dried over magnesium sulphate and filtered. This solution is added to a solution of para-toluenesulphonic acid (3.13 g; 16.5 mmoles) in ethyl acetate (75 ml). The reaction mixture is brought to a temperature of 0° C., and stirring is continued for 30 min. The suspension obtained is filtered; The precipitate is washed with 4×25 ml of tert-butyl methyl ether, then dried. The desired compound is obtained as a yellow powder.

Yield: 89%

Physical characteristics:

m.p.° C.: 176° C. (dec.);

NMR $^1$H: (CD$_3$OD); 1.54 ppm (s; 6H); 2.35 ppm (s; 3H); 3.49 ppm (s; 2H); 7.10–7.47 ppm (m; 3H); 7.21 ppm (d; 2H, J=8 Hz); 7.69 ppm (d; 2H, J=8 Hz); 7.78 ppm (m; 1H).

NMR $^{13}$C: (CD$_3$OD); 21.31 ppm; 27.58 ppm; 40.75 ppm; 49.64 ppm; 127.37 ppm; 129.72 ppm; 130.00 ppm; 130.14 ppm; 130.56 ppm; 131.03 ppm; 139.22 ppm; 142.08 ppm; 143.76 ppm; 145.55 ppm.

MS: (FAB$^+$, para-nitrobenzyl alcohol); 457/455 (M$^{++}$-H$^+$, 67%); 230 (76%); 228 (100%); 226 (53%); 212 (38%); 197 (31%); 154 (48%); 136 (45%).

HRMS: calc. for C20H29N2Se2 (M$^{++}$-H$^+$): 457.0661. exp.: 457.0665.

Example 4

Preparation of di[2-[2'-(1'-amino-2'-methyl)propyl]-4-methoxy]phenyl-diselenide

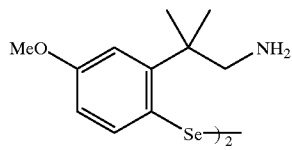

The 4,4-dimethyl-6-methoxybenzisoselenazine derivative BXT 51077 (256 mg; 1 mmol) is dissolved in anhydrous methanol (5 ml). A preparation of this compound has been described in Example 11 of the application WO-A-95/27706. Sodium borohydride (9.5 mg; 0.25 mmoles) is added; then the reaction mixture is stirred for 30 min; at ambient temperature and under air. The methanol is evaporated under reduced pressure. The residue is taken up into 20 ml of water, then extracted with 2×20 ml of dichloromethane. The organic phases are combined, washed with 20 ml of a saturated sodium chloride solution, dried over sodium sulphate and filtered. The solvent is evaporated off under reduced pressure. The desired compound is obtained as an orange oil, in a mixture with 3% of starting material, BXT 51077.

Yield: 82%

(Beware: the product dissolved in organic solvents, such as, for example dichloromethane, slowly oxidises in air to give the starting material, BXT 51077.)

Physical characteristics:

NMR $^1$H: (CDCl$_3$); 0.8 ppm (bs; 2H); 1.34 ppm (s; 6H); 3.06 ppm (s; 2H); 3.74 ppm (s; 3H); 6.60 ppm (dd; 1H, J=8.5–2.5 Hz); 6.84 ppm (d; 1H, J=2.5 Hz); 7.65 ppm (d; 1H, J=8.5 Hz).

This product contains 3% of BXT 51077 according to the comparative integration of the small supplementary signal at 1.24 ppm.

NMR $^{13}$C: (CDCl$_3$); 28.57 ppm; 42.77 ppm; 52.42 ppm; 55.42 ppm; 111.64 ppm; 116.26 ppm; 120.87 ppm; 140.25 ppm; 149.56 ppm; 160.11 ppm.

NMR $^{77}$Se: (CH$_3$SeCH$_3$); 521 ppm (signals of weak intensity at 694 ppm (corresponding to BXT 51077) and 345 ppm).

MS: (CI; isobutane); 517 (MH$^+$; 27%); 258 (100%).

Example 5

Preparation of di[2-[2'-(1'-methylamino-2'-methyl) propyl]-phenyl]-diselenide: BXT 51109

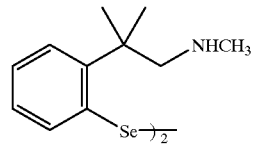

5A/ Preparation of 2,4,4-trimethyl-benzisoselenazine: BXT 51112

The 4,4-dimethylbenzisoselenazine derivative BXT 51072 (452 mg; 2 mmoles) (see Example 8 of WO-A-95/27706) is dissolved in 4 ml of tert-butyl methyl ether. Methyl para-toluenesulphonate (372 mg; 2 mmoles) is added, then the solution is refluxed for 14h. The reaction mixture, brought to ambient temperature, is diluted with tert-butyl methyl ether (20 ml), then extracted with hydrochloric acid (1N; 3×15 ml). The aqueous phases are combined. After making it alkaline (pH=12), the aqueous phase is extracted with tert-butyl methyl ether (3×20 ml). The organic phases are combined, washed with 20 ml of a saturated sodium chloride solution, dried over sodium sulphate and filtered. The solvent is evaporated off under reduced pressure. The desired compound is obtained as a yellow oil after purification by liquid chromatography on a silica column (eluent: cyclohexane-ethyl acetate 9/1).

Yield: 47%

Physical characteristics:

NMR $^1$H: (CDCl$_3$); 1.33 ppm (bs, 6H); 2.78 ppm (s; 3H); 3.06 ppm (s; 2H); 7.0–7.13 ppm (m; 3H); 7.37–7.46 ppm (m; 1H).

NMR $^{13}$C: (CDCl$_3$); 29.85 ppm: 37.05 ppm; 48.51 ppm; 72.11 ppm; 126.09 ppm; 126.30 ppm; 126.85 ppm; 127.85 ppm; 129.69 ppm; 142.64 ppm.

MS: (EI, 70 eV); 241 (M$^+$; 100%); 198 (62%), 183 (76%), 115 (40%).

5B/ Preparation of di[2-[2'-(1'-methylamino-2'-methyl) propyl]-phenyl]-diselenide: BXT 51109

The preceding derivative BXT 51112 (140 mg; 0.58 mmol) is dissolved in anhydrous methanol (5 ml). Sodium borohydride (5.5 mg; 0.145 mmole) is added; then the reaction mixture is stirred for 30 min., at ambient temperature and under air. The methanol is evaporated under reduced pressure. The residue is taken up into 20 ml of hydrochloric acid (1N), then washed with 3×10 ml of tert-butyl methyl ether. The aqueous phase is made alkaline, then extracted with 3×20 ml of dichloromethane. The organic phases are combined, washed with 20 ml of a saturated sodium chloride solution, dried over sodium sulphate and filtered. The solvent is evaporated under reduced pressure. The desired compound is obtained as an orange oil.

(Beware, the product dissolved in organic solvents, such as, for example dichloromethane, slowly oxidises to give the starting material BXT 51112.)

Yield: 75%

Physical characteristics:

NMR $^1$H: (CDCl$_3$); 1.41 ppm (s; 6H); 2.05 ppm (bs; 1H); 2.23 ppm (s; 3H); 3.02 ppm (s; 2H); 7.0–7.20 ppm (m; 2H); 7.83 ppm (dd; 1H, J=8–1.5 Hz); 7.83 ppm (dd; 1H, J=8–1.5 Hz).

NMR $^{13}$C: (CDCl$_3$); 28.70 ppm; 37.27 ppm; 41.28 ppm; 62.27 ppm; 127.91 ppm; 128.18 ppm; 129.54 ppm; 130.36 ppm; 136.37 ppm; 146.68 ppm.

MS: (CI, isobutane); 485 (MH$^+$; 68%); 242 (100%).

Example 6

Preparation of di[2-[2'-(1'-methylamino-2'-methyl) propyl]-phenyl]-diselenide dihydrochloride: BXT 51130

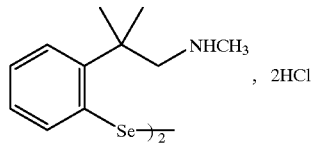

This compound is obtained, according to a method very similar to that of Example 2 from the preceding derivative (BXT 51112) as a yellow-orange powder.

Yield: 89%

Physical characteristics:

m.p.° C.: 260° C. (dec.);

NMR $^1$H: (CD$_3$OD); 1.57 ppm (s; 6H); 2.56 ppm (s; 3H); 3.57 ppm (s;2H); 7.24 ppm (td; 1H, J=8-8-1.5 Hz); 7.37 ppm (td; 1H, J=8-8-1.5 Hz); 7.47 ppm (dd; 1H, J=8-1.5 Hz); 7.85 ppm (dd; 1H, J=8-1.5 Hz).

NMR $^{13}$C: (CD$_3$OD); 27.98 ppm; 35.20 ppm; 40.76 ppm; 59.66 ppm; 129.56 ppm; 130.18 ppm; 130.76 ppm; 131.29 ppm; 139.90 ppm; 145.56 ppm.

Example 7

Preparation of di[2-[2'-(1'-dimethylamino-2'-methyl) propyl]-phenyl]-diselenide: BXT 51110

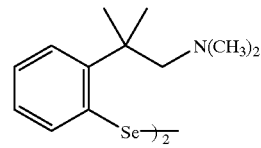

The derivative BXT 51109 obtained in situ, by the method of Example 5/B from BXT 51112 (360 mg; 1.5 mmoles) is dissolved under nitrogen in tert-butyl methyl ether (6 ml). Methyl para-toluenesulphonate (335 mg; 1.8 mmoles) is added, stirring is then continued for 24 h at ambient temperature. Sodium hydroxide solution (1N; 20 ml) is added, then the mixture is extracted with 2×20 ml of dichloromethane. The organic phases are combined, washed with 20 ml of a saturated sodium chloride solution, dried over sodium sulphate and filtered. The solvent is evaporated under reduced pressure. The desired product is obtained as an orange oil after purification by liquid chromatography on a silica column (eluent gradient: cyclohexane-ethyl acetate 20/1 then methanol/triethylamine 100/1).

Yield: 69%

Physical characteristics:

NMR $^1$H: (CD$_3$OD); 1.42 ppm (s; 6H); 2.05 ppm (s; 6H); 2.7 ppm (bs; 2H); 7.02 ppm (td; 1H, J=7.5-7.5-1.5 Hz); 7.14 ppm (td; 1H, J=7.5-7.5-1.5 Hz); 7.33 ppm (dd; 1H, J=7.5-1.5 Hz); 7.89 ppm (dd; 1H, J=7.5-1.5 Hz).

NMR $^{13}$C: (CDCl$_3$); 28.62 ppm; 41.53 ppm; 48.01 ppm; 70.51 ppm; 127.32 ppm; 127.50 ppm; 133.92 ppm; 137.14 ppm; 146.85 ppm. MS: (FAB$^+$; para-nitrobenzyl alcohol); 513 (MH$^+$; 20); 256 (100%); 154 (50%); 136 (40%).

Example 8

Preparation of di[2-[2'-( 1'-trimethylammonium-2'-methyl)propyl]-phenyl]-diselenide di-paratoluenesulphonate: BXT 51111

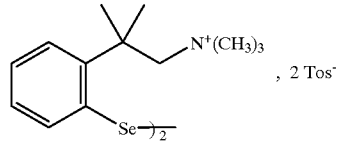

The preceding derivative (102 mg; 0.2 mmol) is dissolved in tert-butyl methyl ether (4 ml). Methyl para-toluenesulphonate (93 mg; 0.5 mmol) is added, then the mixture is refluxed. After 24 h, the reaction mixture, brought to ambient temperature, is diluted with tert-butyl methyl ether (20 ml), then extracted with water (3×15 ml). The aqueous phases are combined and washed with tert-butyl methyl ether (10 ml). The water is evaporated under reduced pressure. The desired product is obtained first as an orange oil. For the crystallisation, the oil is taken up into ethanol (1 ml), then ethyl acetate is added (20 ml). The suspension obtained is filtered and the precipitate washed with 2×5 ml of tert-butyl methyl ether. Thus the desired product is obtained as a yellow powder.

Yield: 48%

Physical characteristics:

m.p.° C.: 203° C. (dec.);

NMR ¹H: (CD₃OD); 1.69 ppm (s; 6H); 2.35 ppm (s; 3H); 2.91 ppm (s; 9H); 4.10 ppm (s; 2H); 7.22 ppm (d; 2H, J=8.5 Hz); 7.27 ppm (td; 1H, J=8-8-1.5 Hz); 7.41 ppm (td; 1H, J=8-8-1.5 Hz); 7.61 ppm (dd; 1H, J=8–1.5 Hz); 7.69 ppm (d; 2H, J=8.5 Hz); 7.89 ppm (dd; 1H, J=8–1.5 Hz).

NMR ¹³C: (CD₃OD); 21.35 ppm; 31.01 ppm; 42.89 ppm; 56.27 ppm; 74.92 ppm; 127.31 ppm; 130.20 ppm; 130.35 ppm; 130.56 ppm; 131.25 ppm; 131.45 ppm; 139.70 ppm; 142.09 ppm; 144.04 ppm; 145.69 ppm.

MS: (FAB⁺, glycerol); 713 ((M-Tos)⁺; 30%); 271 (M⁺⁺-2Tos; 50%); 256 (80%); 212 (100%); 197 (85%); 130 (100%); 91 (50%).

Example 9

Preparation of di [3-[2'-(1'-amino-2'-methyl) propyl]-2-thienyl] diselenide: BXT 51099

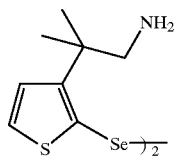

A/ Preparation of 2-bromo-3-bromomethyl-thiophene:

This compound is prepared from 2-bromo-3-methyl-thiophene (1.85 g; 10.4 mmoles) according to a method identical to that described in the literature by E. Campaigne and W. M. Lesuer (J. Am. Chem. Soc., 1949, 71 333–335), and obtained as a colourless oil (2.45 g). The product is used as such in the next step.

Yield: 95%

Physical characteristics:

NMR ¹H: (CDCl₃); 4.43 ppm (s, 2H); 6.98 ppm (d, 1H, J=5.7 Hz); 7.24 ppm (d, 1H, J=5.7 Hz).

B/ Preparation of 3-(2-bromo)-thienyl-acetonitrile:

A round-bottomed flask, containing the preceding bromine derivative (2.10 g; 8.2 mmoles) dissolved in methanol (8 ml), is cooled in a water bath. Under an inert atmosphere, sodium cyanide (0.610 g; 12.3 mmoles) is added all at once. The mixture is left for 4 hours, at ambient temperature. The solvent is evaporated under reduced pressure. The residue is taken up into 15 ml of water and extracted with 2×15 ml of dichloromethane. The organic phases are combined, washed with water, then with a saturated sodium chloride solution, dried over magnesium sulphate, then filtered. After evaporation of the solvent and chromatography on a silica column (eluent gradient pure cyclohexane, then cyclohexane/ethyl acetate (90/10)), the desired product is obtained as a pale yellow oil (1.05 g).

Yield: 64%

Physical characteristics:

NMR ¹H: (CDCl₃); 3.64 ppm (s, 2H); 7.01 ppm (d, 1H, J=5.8 Hz); 7.31 ppm (d, 1H, J=5.8 Hz).

NMR ¹³C: (CDCl₃); 18.62 ppm (E); 112.28 ppm (E); 117.12 ppm (E); 127.50 ppm (O); 128.03 ppm (O); 129.80 ppm (P).

MS: (EI; 70eV); 203/201 (M⁺·; 45); 122 (M-Br; 100); 98 (60).

C/ Preparation of 2-[3'-(2'-bromo)-thienyl]-2-methyl-propionitrile:

To a suspension of NaH (0.140 g; 4 mmoles) in anhydrous DMF (1 ml), kept at -10° C. under an inert atmosphere, is added slowly (~5–10 minutes), a solution containing the preceding derivative (0.202 g; 1 mmole) and methyl iodide (0.570 g, 4 mmoles) in anhydrous DMF (1.5 ml). The reaction mixture is added at 0° C. for one hour, then at ambient temperature for about 2 hours. The residue is taken up into 10 ml of water and extracted with 2×10 ml of ethyl acetate. The organic phases are combined, washed with 3×10 ml of water, then with a saturated sodium chloride solution, dried over magnesium sulphate, then filtered. The desired product is obtained, after evaporation of the solvent, as a yellow brown oil (0.240 g). It will be used as such in the next step.

Yield: quantitative

Physical characteristics:

NMR ¹H: (CDCl₃); 1.80 ppm (s, 6H); 6.94 ppm (d, 1H, J=5.9 Hz); 7.24 ppm (d, 1H, J=5.9 Hz).

NMR ¹³C: (CDCl₃); 27.35 ppm; 33.68 ppm; 109.74 ppm; 122.97 ppm; 126.39 ppm; 126.54 ppm; 138.32 ppm.

MS: (EI; 70eV) 231/229 (M⁺·; 30); 216/214 (M-15; 70); 153/151 (M-Br; 45); 125/123 (42); 97 (100).

D/ Preparation of 2-[3'-(2'-bromo)-thienyl]-2-methyl-propylamine:

The derivative, prepared in Example 9/C, (0.230 g; 1 mmole) is dissolved in anhydrous THF (1 ml), under nitrogen. A solution of aluminium hydride AlH₃ in anhydrous THF (1.5 M; 1.0 ml; 1.5 mmoles) is added slowly to the reaction mixture at ambient temperature. The mixture is refluxed for 2 hours. Brought to ambient temperature, the medium is first hydrolysed, with 1 to 2 ml of water, then with 2 ml of a 2N solution of HCl. After evaporation of solvents, the residue is taken up into 5 ml of a 2N solution of HCl and extracted with 3×10 ml of TBME. The aqueous phase is made alkaline (pH=12), then extracted with 3×6 ml of ethyl acetate. The organic phases are combined, washed with 2×10 ml of water, then with a saturated sodium chloride solution, dried over magnesium sulphate, then filtered. The desired product is obtained after evaporation of the solvent, as a yellow oil (0.125 g).

Yield: 53%

Physical characteristics:

NMR ¹H: (CDCl₃); 1.12 ppm ( bs, —NH2); 1.38 ppm (s, 6H); 2.98 ppm (s, 2H); 6.84 ppm (d, 1H, J=5.8 Hz); 7.16 ppm (d, 1H, J=5.8 Hz).

NMR ¹³C: (CDCl₃); 26.38 ppm; 40.15 ppm; 52.19 ppm; 107.04 ppm; 125.61 ppm; 129.36 ppm; 145.17 ppm.

MS: (CI; isobutane); 236/234 (MH+; 100); 220/218 (M-NH2; 5); 154 (M-Br; 47); 125/123 (12).

E/ Preparation of 4,4-dimethyl-thieno-[3,2-e]-isoselenazine:

To a solution of potassium selenocyanate (1.0 g; 6.9 mmoles) in anhydrous DMF (7 ml), is added the derivative prepared as in Example 9/D (0.702 g; 3 mmoles). To this solution, cooled to 5° C. and under an inert atmosphere, are then added copper I iodide (0.570 g; 3 mmoles), then triethylamine (0.900 g; 9 mmoles). The reaction mixture rapidly becomes deeply coloured, and is thus kept stirred for 17 hours, at ambient temperature and under nitrogen. 70 ml of an aqueous sodium cyanide solution are added (0.560 g; 11.4 mmoles) such that the copper iodide is complexed out, thus facilitating the two phases. After decantation, the aqueous phase is extracted with 70 ml of ethyl acetate. The organic phase is washed with 5×50 ml of water, then with 2×50 ml of a saturated sodium chloride solution, dried over magnesium sulphate, then filtered. The desired product is obtained after evaporation of the solvent and chromatography on a silica column (eluent cyclohexane/ethyl acetate (95/5)) as light yellow crystals (0.390 g).

Yield: 56%

Physical characteristics
m.p. ° C.: 51.6–51.8° C. (hexane/ethyl acetate: 75/1);
NMR ¹H: (CDCl₃); 1.21 ppm (s, 6H); 3.18 ppm (s, 2H); 3.29 ppm (bs, —NH); 7.05 ppm (d, 1H, J=5.2 Hz); 7.27 ppm (d, 1H, J=5.2 Hz).
NMR ¹³C: (CDCl₃); 28.63 ppm (O); 33.69 ppm (E); 61.50 ppm (E); 119.78 ppm (E); 123.93 ppm (O); 127.18 ppm (O); 141.84 ppm (P).
NMR ⁷⁷Se: (CH₃SeCH₃); 737.0 ppm.
MS: (EI; 70 eV); 233 (M³⁰ ⁺; 82); 204 (79); 189 (100); 124 (22); 97 (17).
The product obtained BXT 51097 is of the formula below:

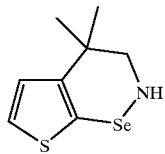

F/ Said 4,4-dimethylthieno-[3,2-e]isoselenazine derivative BXT 51097 (0.114 g; 0.50 mmoles), is dissolved in methanol (5 ml), at ambient temperature. To this solution cooled at 0° C., sodium borohydride is added (0.100 g; 2.5 mmoles). The reaction mixture is allowed to attain ambient temperature. After 15 to 20 minutes, the solvent is evaporated under reduced pressure. The residue, taken up into ethyl acetate, is washed 3-4 times with a saturated sodium chloride solution, then dried over magnesium sulphate and filtered. After evaporation of the solvent under reduced pressure, the desired product is obtained (BXT 51099), as a yellow oil (0.080 g).
Yield: 35%.
Physical characteristics:
NMR ¹H: (CDCl₃); 1.34 ppm (s, 6H); 2.92 ppm (s, 2H); 6.96 ppm (d, 1H, J=5.4 Hz); 7.36 ppm (d, 1H, J=5.4 Hz).
NMR ¹³C: (CDCl₃); 27.78 ppm; 41.08 ppm; 53.96 ppm; 119.73 ppm; 129.95 ppm; 131.07 ppm; 152.48 ppm.
NMR ⁷⁷Se: (CH₃SeCH₃); 509.3 ppm
MS: (EI; 70eV); 233 (M⁺·/2; 65); 204 (65); 189 (100); 124 (30); 97 (27).

Example 10

Preparation of di[2-[2'-(1'-amino-2'-methyl) propyl]-3-thienyl]-diselenide: BXT 51104

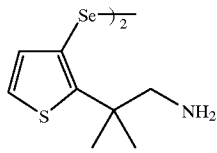

A/ Preparation of 3-bromo-2-hydroxymethyl-thiophene:
2-(3-bromothienyl)carboxylic acid (7 g; 34 mmoles) is dissolved in 25 ml of anhydrous THF. A solution of aluminium hydride AlH₃ in anhydrous THF (2 M; 42 ml; 84 mmoles) is added slowly at a temperature of 0° C. At the end of the addition, the reaction mixture is refluxed for 3 h. After cooling to 0° C., water (200 ml), then hydrochloric acid (1N, 150 ml) are added. The mixture is decanted, and the aqueous phase extracted with 3×150 ml of tert-butyl methyl ether. The organic phases are combined, then washed with 150 ml of a saturated sodium chloride solution, dried over magnesium sulphate and filtered. The solvent is evaporated under reduced pressure. The desired product is obtained as a brown oil and is used as such for the next step.

Yield: 95%
Physical characteristics:
NMR ¹H: (CD₃OD); 4.69 ppm (s; 2H); 6.95 ppm (d; 1H, J=5.2 Hz); 7.39 ppm (d; 1H, J=5.2 Hz).
NMR ¹³C: (DMSO-d₆); 57.80 ppm; 106.28 ppm; 126.11 ppm; 129.80 ppm; 141.15 ppm.
MS: (EI, 70 eV); 194/192 (M⁺·; 80%); 177/175 (30%); 113 (50%); 98 (60%); 85 (100%).

B/ Preparation of 3-bromo-2-chloromethyl-thiophene:
The preceding derivative (6.2 g; 32 mmoles) is dissolved in anhydrous dichloromethane (180 ml). Thionyl chloride (5.7 g; 3.5 ml; 48 mmoles) is added slowly, then stirring is kept up for 18h at ambient temperature. The reaction mixture is poured into 200 ml of water, then decanted. The aqueous phase is extracted with 2×100 ml of tert-butyl methyl ether. The organic phases are combined, washed with a saturated sodium bicarbonate solution (200 ml), dried over magnesium sulphate and filtered. The solvent is evaporated off under reduced pressure. The desired product is obtained as a brown oil and is used as such for the next step.
Yield: 90%
Physical characteristics:
NMR ¹H: (CDCl₃); 4.75 ppm (s; 2H); 6.95 ppm (d; 1H, J=5.2 Hz); 7.30 ppm (d; 1H, J=5.2 Hz).
NMR ¹³C: (CDCl₃); 39.5 ppm; 112.5 ppm; 127.5 ppm; 131.0 ppm; 135.0 ppm.
MS: (EI, 70 eV); 212 (M⁺·; 35%); 177(100%); 96 (20%).

C/ Preparation of 2-(3-bromo)-thienyl-acetonitrile:
The preceding derivative (6 g; 28 mmoles) is dissolved in DMSO (100 ml). Sodium cyanide (2 g; 41 mmoles) is added, then stirring is kept up for 2 h. The reaction mixture is poured into 200 ml of water. The mixture is extracted with 3×100 ml of tert-butyl methyl ether, then 2×100 ml of dichloromethane. The organic phases are combined, washed with 3×200 ml of water, dried over magnesium sulphate and filtered. The solvent is evaporated off under reduced pressure. The residue is taken up into 400 ml of cyclohexane and washed with 4×100 ml of water. The organic phase is dried over magnesium sulphate and filtered. The solvent is evaporated under reduced pressure. The desired product is obtained as a colourless oil after distillation of the residue in a Kugelrohr distillation apparatus (T=200° C., p=0.1 mbar).
Yield: 60%
Physical characteristics:
NMR ¹H: (CDCl₃); 3.84 ppm (s; 2H); 7.00 ppm (d; 1H, J=5.2 Hz); 7.31 ppm (d; 1H, J=5.2 Hz).
NMR ¹³C: (CDCl₃); 18.39 ppm; 112.29 ppm; 116.30 ppm; 126.37 ppm; 126.65 ppm; 130.92 ppm.
MS: (EI, 70 eV); 203/201 (M⁺·; 29%); 122 (100%); 98 (40%).

D/ Preparation of 2-[2'-(3'-bromo-thienyl)]-2-methyl-propionitrile:
This compound is obtained according to a method very similar to that of Example 9/C from the preceding derivative as a yellow oil.
Yield: 90%
Physical characteristics:
NMR ¹H: (acetone-d₆); 1.77 ppm (s; 6H); 7.02 ppm (d; 1H, J=5.2 Hz); 7.44 ppm (d; 1H, J=5.2 Hz).
NMR ¹³C: (CDCl₃); 5 20.11 ppm; 33.90 ppm; 109.68 ppm; 122.15 ppm; 124.39 ppm; 133,21 ppm; 137.27 ppm.
MS: (EI, 70 eV); 231/229 (M⁺·; 50%); 216/214 (100%); 189/187 (45%).

E/ Preparation of 2-[2'-(3'-bromo-thienyl)]-2-methyl-propylamine:
This compound is obtained according to a method very similar to that of Example 9/D from the preceding derivative as a pale yellow oil.

Yield: 80%

Physical characteristics:

NMR ¹H: (CDCl₃); 1.10 ppm (bs; 2H); 1.44 ppm (s; 6H); 3.06 ppm (s; 2H); 6.93 ppm (d; 1H, J=5.2 Hz); 7.07 ppm (d; 1H, J=5.2 Hz).

NMR ¹³C: (CDCl₃); 26.45 ppm; 40.76 ppm; 51.78 ppm; 105.89 ppm; 123.01 ppm; 133,26 ppm; 145.00 ppm.

MS: (CI, isobutane); 236/234 (MH⁺; 40%); 154 (25%); 93 (100%).

F/ Preparation of 4,4-dimethyl-thieno-[2,3-e]-isoselenazine: BXT 51103

This compound is obtained according to a method very similar to that of Example 9/E from the preceding derivative as a yellow oil, which crystallises at −20° C.

Yield: 54%

Physical characteristics:

m.p.° C.: 31° C.;

NMR ¹H: (CDCl₃); 1.33 ppm (s; 6H); 3,20 ppm (s; 2H); 3.30 ppm (bs; 1H); 6.68 ppm (d; 1H, J=5.3 Hz); 7.24 ppm (d; 1H, J=5.3 Hz).

NMR ¹³C: (CDCl₃); 30.02 ppm; 34.16 ppm; 61.35 ppm; 119.64 ppm; 122.89 ppm; 124.57 ppm; 139.89 ppm.

NMR ⁷⁷Se: (CH₃SeCH₃); 727.0 ppm.

MS: (EI, 70 eV); 233 (M³⁰ ⁺; 86%); 203 (10%); 189 (40%);153 (20%), 124 (40%); 77 (35).

The product obtained BXT 51103 is of the formula below:

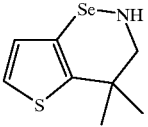

G/ The compound BXT 51104 of the invention is obtained, according to a method very similar to that of Example 9 from said 4,4-dimethylthieno[2,3-e]isoselenazine BXT 51103 derivative as a yellow oil.

(Beware, the product dissolved in organic solvents, such as, for example dichloromethane, slowly oxidises to give the starting material BXT 51103.)

Yield: 95%

Physical characteristics:

NMR ¹H: (CDCl₃); 1.2 ppm (bs, 2H); 1.37 ppm (s, 6H); 2.93 ppm (s, 2H); 7.06 ppm (d, 1H, J=5.3 Hz); 7.13 ppm (d, 1H, J=5.3 Hz).

NMR ¹³C: (CDCl₃); 27.74 ppm; 41.35 ppm; 53.44 ppm; 119.40 ppm; 122.51 ppm; 136.86 ppm; 151.71 ppm.

NMR ⁷⁷Se: (CH₃SeCH₃); 446.6 ppm.

MS: (CI, isobutane); 469 (MH⁺; 40%); 292 (20%); 276 (30%); 250 (30%); 234 (100%); 154 (30%).

Example 11

Preparation of S-(N-acetyl-L-cysteinyl)-[2-[2'-(1'-amino-2'-methyl)-propyl]-phenyl]-selenide:

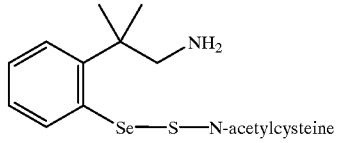

The 4,4-dimethylbenzisoselenazine derivative BXT 51072 (226 mg; 1 mmole) (see Example 8 of WO-A-95/27706) is dissolved in anhydrous methanol (5 ml). N-acetylcysteine (163 mg; 1 mmol) is added. After a few seconds, a yellow precipitate is formed and stirring is continued for 20 min. The suspension obtained is filtered and this precipitate is washed with methanol (10 ml). The desired compound is obtained as very fine yellow crystals.

Yield: 77%

Physical characteristics:

m.p.° C.: 155° C. (dec.);

NMR ¹H: (CD₃OD); 1.53 ppm (s; 6H); 1.86 ppm (s; 3H); 3.04 ppm (dd; 1H, J=14–9.5 Hz); 3,29 ppm (m; partially superimposed with the peak of CHD₂OD); 3.65 ppm (d; 1H, J=13 Hz); 3.91 ppm (d; 1H, J=13 Hz); 4.19 ppm (dd; 1H, J=9.5-3.5 Hz); 7.22–7.44 ppm(m; 3H); 8.11 ppm(m; 1H).

NMR ¹³C: (CD₃OD); 22.62 ppm; 28.52 ppm; 28.86 ppm; 40.60 ppm; 40.73 ppm; 47.32 ppm; 56.20 ppm; 129.39 ppm; 130.01 ppm; 130.30 ppm; 132.72 ppm; 135.14 ppm; 143.52 ppm; 173.42 ppm; 177.57 ppm.

MS: (FAB; glycerol); 391 (MH⁺; 96%); 228 (100%); 185 (100%); 150 (40%); 457 (20%).

Example 12

Preparation of S-glutathionyl-[2-[2'-(1'-amino-2'-methyl)-propyl]-phenyl]-selenide: BXT 51113

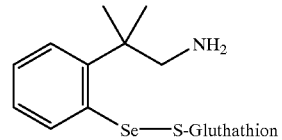

A solution of reduced glutathione (154 mg; 0.5 mmol) in 25 ml of aqueous ethanol (7/3 v/v) is added to a solution of 4,4-dimethylbenzisoselenazine BXT 51072 (226 mg; 1 mmol) (see Example 8 of WO-A-95/27706) at ambient temperature. Stirring is kept up for 5 min.; then the solvent is evaporated under reduced pressure. The residue is taken up into 20 ml of aqueous methanol (1/2, v/v) is filtered. The filtrate is evaporated under reduced pressure, then the residue is taken up a second time in aqueous methanol, filtered, and the solvent is evaporated under reduced pressure. The desired product is obtained first as a very viscous oil, which crystallises slowly giving pale yellow crystals.

Yield: 94%

Physical characteristics:

m.p.° C.: 175° C. (dec.);

NMR ¹H: (CD₃OD /D₂O, 1/1): 1.43 ppm (s; 6H); 1.93 ppm (m; 2H); 2.32 ppm (m; 2H); 2.99 ppm (dd; 1H, J=12 −10 Hz); 3.25 ppm (dd; 1H, J=13–4 Hz); 3.50 ppm (m; 4H); 3.68 ppm (d; 1H, J=13 Hz); 4.70 ppm (dd; 1H, J=10–4 Hz); 7.14-7.57 ppm (m; 3H); 7.94 ppm (m; 1H).

NMR ¹H: (DCl/D₂O, 1N): 1.25 ppm (s; 3H); 1.27 ppm (s; 3H); 1.83 ppm (m; 2H); 2.20 ppm (m; 2h); 2.87 ppm (dd; 1H, J=14–9.5 Hz); 3.08 ppm (dd; 1H, J=14–4.5 Hz); 3.27 ppm (d; 1H, J=14 Hz); 3.41 ppm (d; 1H, J=14 Hz); 3.65 ppm (s; 2H); 3.79 ppm (t; 1H, J=6.5 Hz)4.19 ppm (dd; 1H, J=9.5–4.5 Hz); 7.0–7.2 ppm (m; 3H); 7.76 ppm (m; 1H).

MS: (FAB, glycerol); 551 (4%); 533 (M-H⁺; 5%); 459 (10%); 306 (50%); 275 (100%).

II/EXAMPLES OF SYNTHESIS OF COMPOUNDS OF GENERAL FORMULA II

Series wherein $R_5$32 hydrogen:

Example 13

Preparation of bis-4(5)-[2-phenyl-4(5)-seleno-1H-imidazole]: BXT 51038

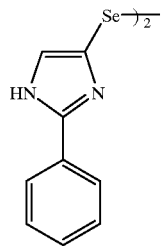

A/ Preparation of 2-phenyl-1-[2'-(trimethylsilyl) ethoxymethyl]-imidazole:

This derivative is prepared from 2-phenyl-1H-imidazole (1.0 g; 6.9mmoles) and (trimethylsilyl)ethoxymethyl chloride (1.33 g; 7.6 mmoles) according to method (1), described in the literature by T. P. Demuth, Jr, et al. (J. Org. Chem., 1992. 57. 2963–65). The crude reaction product (2.8 g) is purified by chromatography on a silica column (eluent: cyclohexane-ethyl acetate; 6/4). The desired product is obtained as a colourless oil (1.5 g).

Yield: 80%

Physical characteristics:

NMR $^1$H: (CDCl$_3$); –0.05 ppm (s, 9H); 0.87 ppm (t, 2H, J=10.50 Hz); 3.52 ppm (t, 2H, J=10.50 Hz); 5.26 ppm (s, 2H); 7.10 ppm (d, 1H, J=1.3 Hz); 7.12 ppm (d, 1H, J=1.3 Hz); 7.42 ppm (m, 3H); 7.75 ppm (m, 2H).

NMR $^{13}$C: (CDCl$_3$); –1.29 ppm(O); 18.0 ppm (E); 66.93 ppm (E); 75.99 ppm (E); 121.96 ppm(O); 128.27 ppm(O); 129.23 ppm(O); 129.56 ppm(O); 129.89 ppm (0); 131.46 ppm (O); 148.91 ppm (E).

MS: (EI; 70eV); 274 (M$^{30}$ *; 32); 216 (55); 158 (38); 73 (100).

B/ Preparation of bis-5-[2-phenyl-1-[2'-(trimethylsilyl) ethoxymethyl]-5-seleno-imidazole]:

A solution of selenium I chloride (0.114 g; 0.51 mmoles) in anhydrous dichloromethane (1 ml) is added dropwise, at 35–40° C. and with stirring, to a solution of the preceding derivative (0.140 g; 0.51 mmoles) in the same solvent (1 ml). After a few minutes at this temperature, the red reaction mixture becomes bright yellow-orange. Then the mixture is allowed to attain ambient temperature. After one night, the yellow solution is neutralised with the aid of a saturated sodium hydrogen carbonate solution, then extracted with ethyl ether. The organic phases are combined, washed with a saturated sodium chloride solution, then dried over magnesium sulphate. After evaporation of the solvent under reduced pressure, the residual product is purified by chromatography on a silica column (eluent: cyclohexane-ethyl acetate; 7/3). The desired product is obtained as a bright yellow paste (0.210 g).

Yield: 58%

Physical characteristics:

NMR $^1$H: (CDCl$_3$); –0.05 ppm (s, 9H); 0.88 ppm (t, 2H, J=10.50 Hz); 3.53 ppm (t, 2H, J=10.50 Hz); 5.25 ppm (s, 2H); 7.29 ppm (s, 1H); 7.46 ppm (m, 3H); 7.80 ppm (m, 2H).

NMR $^{13}$C: (CDCl$_3$); –1.40 ppm; 18.19 ppm; 66.70 ppm; 73.77 ppm; 118.26 ppm; 129.19 ppm; 129.56 ppm; 130.13 ppm; 130.65 ppm; 140;39 ppm; 153.59 ppm.

MS: (CI; isobutane); 707 (MH+; 37); 355 (50); 275 (100).

C/ Preparation of bis-4(5)-[2-phenyl-4(5)-seleno-1H-imidazole]:

The preceding selenide (0.528 g; 0.75 mmoles), in solution in 30ml of a mixture of aqueous hydrofluoric acid and acetonitrile (5/95), is refluxed (≈80° C.) for 22 h. After being cooled, the reaction mixture is neutralised with the aid of sodium hydrogen carbonate. The aqueous phase is extracted 4 times with ethyl acetate (v/v). The organic phases are combined, washed with a saturated sodium chloride solution, then dried over magnesium sulphate. After evaporation of the solvent under reduced pressure, the residual product is purified by chromatography on a silica column (eluent: cyclohexane-ethyl acetate; 6/4). The desired product is obtained as a yellow-orange solid (0.208 g).

Yield: 62%

Physical characteristics:

m.p.° C.: 219–219.5° C. (hexane/ethyl acetate: 1/1);

NMR $^1$H: (CD$_3$OD); 7.24 ppm (s, 1H); 7.43 ppm (m, 3H); 7.86 ppm (m, 2H).

NMR $^{13}$C: (CD$_3$OD); 122.83 ppm (E); 127.24 ppm (O); 130.47 ppm (O); 131.02 ppm (O); 131.12 ppm (E); 151.27 ppm (E).

MS: (EI; 70eV); 446 (M$^{+\cdot}$; 30); 224 (25); 149 (100);

Example 14

Preparation of bis-4(5)-[[2-(4'-carbomethoxy) phenyl]-4(5)-seleno-1H-imidazole]: BXT 51079

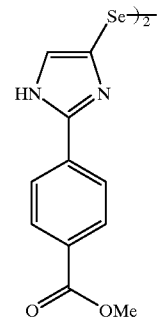

A/ Preparation of [2-[(4'-carbomethoxy)phenyl]-1-[2'-(trimethylsilyl)ethoxymethyl]-imidazole:

The preparation of the intermediate [1-(trimethylsilyl) ethoxymethyl]-imidazole-2-zinc chloride is carried out according to method (2), described in the literature by A. S. Bell, D. A. Roberts, and K. S. Ruddock (Tetrahedron Lett., 1988. 29(39), 5013–16), from 1-(trimethylsilyl) ethoxymethyl-imidazole (6.075 g; 30.8 mmoles), (prepared according to method (1) already cited in Example 13/A), and anhydrous zinc chloride (5.0 g; 36.7 mmoles). The organozinc derivative thus obtained, is used directly for the following coupling reaction and is not isolated.

The suspension of the preceding intermediate [1-(trimethylsilyl) ethoxymethyl]-imidazole-2-zinc chloride, (55 ml; 30.8 mmoles) in anhydrous THF, is treated under nitrogen, with palladium (0) tetrakistriphenylphosphine (0.4g; 0.35mmoles), and methyl 4-bromobenzoate (4.6g; 21.6mmoles) in anhydrous THF (15 ml). The reaction mixture is heated one hour under reflux (~65–70° C.), under nitrogen, then 8 additional hours, after addition of an excess of zinc chloride (8.8g; 61mmoles). The reaction mixture is then treated in a similar manner to the literature (2). After evaporation of the solvent under reduced pressure, the residual product is purified by chromatography on a silica column (eluent gradient: cyclohexane-ethyl acetate 85/15; then ethyl acetate- cyclohexane 95/5; then ethyl acetate-methanol 90/10). The desired product is obtained as a white solid (5.56 g).

Yield: 90%

Physical characteristics:

NMR $^1$H: (CDCl$_3$); 0.002 ppm (s, 9H); 0.94 ppm (t, 2H, J=8.60 Hz); 3.61 ppm (t, 2H, J=8.60 Hz); 3.94 ppm (s, 3H); 5.30 ppm (s, 2H); 7.15 ppm (d, 1H, J=1.42 Hz); 7.18 ppm (d, 1H, J=1.42 Hz); 7.92 ppm (m symmetrical, 2H); 8.12 ppm (m symmetrical, 2H).

NMR $^{13}$C: (CDCl$_3$); −1.3 ppm; 17.99 ppm; 52.55 ppm; 66.95 ppm; 75.93 ppm; 122.94 ppm; 129.16 ppm; 129.62 ppm; 130.38 ppm; 130.73 ppm; 134.96 ppm; 148.017 ppm; 167.38 ppm.

MS: (EI; 70eV); 332 (M$^{30}$ *; 28); 289 (32); 274 (68); 170 (86); 73 (100).

B/ Preparation of bis-5-[[2-(4'-carbomethoxy)phenyl]-1-[2'-(trimethylsilyl)ethoxymethyl]-5-seleno-imidazole]:

The desired product is obtained from the preceding derivative (4.6 g, 14 mmoles) and selenium I chloride (7.6 g, 33.3 mmoles) in anhydrous dichloromethane (80 ml) in following the same procedure as that described in Example 13/B (the temperature of addition of Se$_2$Cl$_2$ is 0° C. in the present case). The desired product is obtained after purification by chromatography on an alumina column (eluent gradient: pure dichloromethane, then dichloromethane/ethyl acetate 90/10, then pure ethyl acetate, then ethyl acetate/methanol 90/10), as a bright yellow solid (2.46 g).

Yield: 43%

Physical characteristics:

NMR $^1$H: (CDCl$_3$); 0.005 ppm (s, 9H); 0.95 ppm (t, 2H, J=9.0 Hz); 3.61 ppm (t, 2H, J=9.0 Hz); 3.96 ppm ( s, 3H); 5.32 ppm (s, 2H); 7.33 ppm (s, 1H); 7.96 ppm(m symmetrical, 2H); 8.15 ppm (m symmetrical, 2H).

NMR $^{13}$C: (CDCl$_3$); 1.6 ppm; 18.26 ppm; 52.65 ppm; 53.75 ppm; 66.98 ppm; 73.86 ppm; 119.11 ppm; 129.39 ppm; 130.46 ppm; 131.45 ppm; 134.60 ppm; 140.569 ppm; 152.47 ppm; 167.18 ppm.

MS: (FAB+; glycerol); 823 (MH$^+$; 85); 743 (M-Se,12); 543 (45); 375 (100).

C/ Preparation of bis-4(5)-[[2-(4'-carbomethoxy)phenyl]-4(5)-seleno-1H-imidazole]:

The preceding selenide (0.260 g; 0.32 mmoles) is treated following the same method as that described in Example 13/C. The desired product is obtained after purification by chromatography on an alumina column (eluent gradient: ethyl acetate/methanol (0.5%, then 1%) as a yellow orange solid (0.108 g).

Yield: 60%

Physical characteristics:

NMR $^1$H: (CD$_3$OD); 3.94 ppm (s, 3H); 7.35 ppm (bs, 1H); 7.97 ppm (m symmetrical, 2H); 8.07 (m symmetrical, 2H)

NMR $^{13}$C: (CD$_3$OD); 52.90 ppm; 126.65 ppm; 126.88 ppm; 126.94 ppm; 131.55 ppm; 131.96 ppm; 135.16 ppm; 166.61 ppm; 168.34 ppm.

MS: (CI; isobutane); 563 (MH+; 2); 483 (M-Se, 1.8); 203 (100).

Example 15

Preparation of bis-4(5)-[2-[(4'-carboxyl)phenyl]-4(5)-seleno-1H-imidazole]: BXT 51043

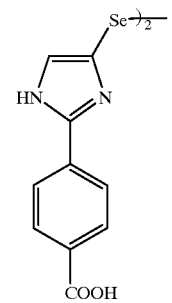

The derivative BXT 51079 (0.080 g; 0.14 mmoles), obtained in the preceding Example, is dissolved in anhydrous THF (16 ml). To this solution cooled at 0° C. is added an aqueous solution (8 ml) of lithium hydroxide (0.075 g, 1.8 mmoles). The reaction is continued for 24 hours at ambient temperature. After the treatment of the crude reaction mixture, according to method (3) described in the literature by D. A. Evans et al., (Tetrahedron., 1988. 17. 5525–5540), the desired product is obtained as a yellow-green solid (0. 154 g).

Yield: 90%

Physical characteristics:

m.p.° C.: ~230° C. (dec);

NMR $^1$H: (CD$_3$OD); 7.28 ppm (bs, 1H); 7.92 ppm (m, 2H); 8.05(m, 2H).

NMR $^{13}$C: (CD$_3$OD); 126.21 ppm; 126.4 ppm; 126.6 ppm; 131.31 ppm; 132.58 ppm; 137.0 ppm; 140.0 ppm; 174.89 ppm;

Example 16

Preparation of bis-4(5)-[2-[4'-carbo(2'-(4'''-methyl-piperazin-1''-yl)ethoxyphenyl)]-4(5)-seleno-1H-imidazole]: BXT 51070

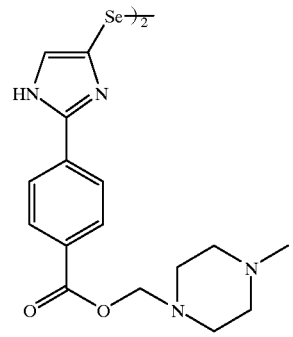

A/ Preparation of bis-5-[[2-(4'-carboxyl)phenyl]-1-[2'-(trimethylsilyl)ethoxymethyl]-5-seleno-imidazole]:

The desired product is obtained from the derivative prepared in Example 14/A (2.1 g, 2.56 mmoles) in solution in anhydrous THF (20 ml), treated with an aqueous solution (10 ml) of lithium hydroxide (0.260 g, 12.3 mmoles) according to method (3) already cited. After a lyophilisation step, the compound is obtained as a yellow crystalline product (2.4 g).

Yield: quantitative

Physical characteristics:

NMR $^1$H: (CD$_3$OD); −0.02 ppm (s, 9H); 0.92 ppm (t, 2H, J=7.7 Hz); 3.60 ppm (t, 2H, J=7.7 Hz); 5.42 ppm (s, 2H); 7.29 ppm (s, 1H); 7.81 ppm (m symmetrical, 2H); 8.11 ppm(m symmetrical, 2H).

NMR $^{13}$C: (CD$_3$OD); 1.6 ppm (O); 18.83 ppm (E); 67.80 ppm (E); 75.24 ppm(E); 120.43 ppm(E); 135.03 (O); 131.11 (O); 132.69 ppm (E); 140.04 (O); 140.89(E); 154,42 ppm (E); 174.52 (E).

MS: (FAB+; glycerol); 795 (MH$^+$; 10); 399 (100).

B/ Preparation of bis-5-[[2-(4'-carbosuccinimidyloxy) phenyl]-1-[2'-(trimethylsilyl)ethoxymethyl]-5-seleno-imidazole].

This derivative is obtained from the preceding product (0.400 g; 0.5 mmoles) and N-hydroxysuccinimide (0.115 g; 1 mmole) according to method described in the literature by G. W. Anderson et al., (J. Am. Chem. Soc., 1964, 86 , 1839) and W. Konig and R. Geiger (Chem. Ber., 1973, 106, 3626). After 72 hours at 25 ° C., the reaction mixture is treated in an identical manner to that described. The solvent is evaporated under reduced pressure, and the crude product is isolated, as a bright yellow-orange solid (0.495 g).

Yield: 76%

Physical characteristics:

NMR $^1$H: (CDCl$_3$); −0.015 ppm (s, 9H); 0.97 ppm (t, 2H, J=8.4 Hz); 2.94 ppm (bs, 4H); 3.66 ppm (t, 2H, J=8.18 Hz); 5.37 ppm (s, 2H); 7.35 ppm (s, 1H); 8.09 ppm (m symmetrical, 2H); 8.27 ppm (m symmetrical, 2H).

MS: (FAB+; para-nitrobenzyl alcohol); 990 (MH$^+$; 14); 495 (MH$^+$/2; 20); 439 (100).

C/ Preparation of bis-5-[2[4'-carbo(2-(4'''-methyl-piperazin-1''-yl)ethoxyphenyl)]-5-seleno-1-[2'-(trimethylsilyl) ethoxymethyl)-1H-imidazole]:

1/—Preparation of N-(2-hydroxyethyl)-N'- methyl-piperazine:

N-methyl-piperazine (10 g, 100 mmoles) and 2-chloroethanol (8.5 g,100 mmoles) are stirred at 100° C. for 4 hours. 250 ml of acetone are added to the very viscous reaction mixture and the resulting suspension is neutralised with 15 ml of triethylamine. After filtration of the triethylammonium chloride, the solvent is evaporated under reduced pressure. The desired compound is obtained after purification by chromatography on an alumina column (eluent: ethyl acetate) as a colourless oil.

Yield: 75%

Physical characteristics

NMR $^1$H: (CDCl$_3$); 2.20 ppm(s, 3H); 2.39 ppm(m, 8H); 2.46 ppm(t, 2H, J=5.5 Hz); 3.41 ppm(bs, 1H); 3.54 ppm(t, 2H, J=5.5 Hz)

2/—Preparation of bis-5-[2[4'-carbo(2''-(4'''-methyl-piperazin-1'-yl)-ethoxyphenyl]-5-seleno-1-[2-(trimethylsilyl)ethoxymethyl)-1H-imidazole].

N-hydroxysuccinimide ester, prepared in Example 17/B (0.270 g, 0.275 mmoles) and dissolved in a minimum of anhydrous THF (2 ml), is mixed with N-2-hydroxyethyl-N'-methylpiperazine (2.15 g, 3.5 mmoles), used here as solvent. After addition at ambient temperature of titanium tetraisopropoxide (0.055 ml, 0.137 mmoles), the reaction mixture is heated at 80° C. for 2 hours. Once the reaction has finished, the THF present in the medium is evaporated, then the excess of alcohol is distilled off under reduced pressure (T=90–100° C./p=0.2 mmHg). The residue is finally purified by chromatography on a basic alumina column—activity I (eluent: ethyl acetate/methanol 95/5). A bright yellow product is isolated (0.113 g).

Yield: 40%

Physical characteristics:

NMR $^1$H: (CDCl$_3$); −0.041 ppm (s, 9H); 0.89 ppm (t, 2H, J=8.14 Hz); 2.31 ppm (s, 3H); 2.62 ppm(m, 8H); 2.83 ppm (t, 2H, J=5.4 Hz); 5.39 ppm (s, 2H); 7.30 ppm (bs, 1H); 7.92 ppm (m symmetrical, 2H); 8.16 ppm(m symmetrical, 2H).

NMR $^{13}$C: (CD$_3$OD); −1.30 ppm(O); 18.86 ppm(E); 45.90 ppm(O); 53.82 ppm(O); 55.71 ppm(E); 57.66 ppm(E); 63.64 ppm(E); 67.90(E); 75.18 (E); 121.0 ppm(E); 130.59 ppm(O); 131.36 ppm(O); 132.99 ppm(E); 135.45 ppm(E); 140.38 ppm(O); 153.41 ppm(E); 167.51 ppm(E).

MS: (FAB+, glycerol); 1047 (MH$^+$; 3.5); 525 (MH$^+$/2; 80); 445 (MH$^+$/2-Se, 58)

D/ Preparation of bis-4(5)-[2-[4'-carbo(2''-(4'''-methyl-piperazin-1''-yl)ethoxy phenyl]-4(5)-seleno-1H-imidazole].

The preceding selenide (0.143 g, 0.137 mmoles) in solution in 14 ml of a mixture of aqueous hydrofluoric acid and acetonitrile (5/95) is refluxed ( 80° C.) for 20 hours. After being cooled, the reaction mixture is treated in the same way as that described in Example 13/C. After having evaporated the solvent under reduced pressure, the residue is then purified by chromatography on a basic alumina column—activity I (eluent gradient: ethyl acetate/methanol 95/5, then ethyl acetate/methanol 90/10). The desired product is obtained as a bright yellow paste (0.049 g).

Yield: 45%

Physical characteristics:

NMR $^1$H: (CD$_3$OD); 2.28 ppm (s, 3H); 2.60 ppm(m, 8H); 2.82 ppm (t, 2H, J=5.4 Hz); 4,48 ppm (s,2H); 7.33 ppm (bs, 1H); 7.97 ppm (m symmetrical, 2H); 8.10 ppm (m symmetrical, 2H).

NMR $^{13}$C: (CD$_3$OD); 45.67 ppm(O); 53.90 ppm(O); 54.91 ppm(E); 56.66 ppm(E); 62.89 ppm(E) 126.26 ppm(E); 126.53 ppm(O); 130.35 ppm(O); 130.62 ppm(E); 134.15 ppm(E); 149.35 ppm(O); 166.39 ppm(E); 177.52(E).

MS: (FAB+, glycerol); 785 (MH$^+$; 4); 393(MH$^+$/2; 33)

Series wherein R$_5$≠hydrogen:

Example 17

Preparation of bis-5-[2-[(4'-trifluoromethyl)phenyl]-5-seleno-1-methyl-imidazole]: BXT 51045

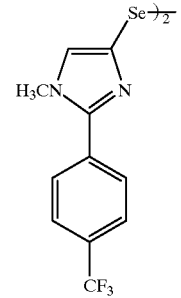

A/ Preparation of 2-[(4'-trifluoromethyl)phenyl]-1-methyl-imidazole:

The preparation of the intermediate 2-(tributylstannyl)-1-methyl-imidazole is carried out according to method described by K. C. Molloy. et al., (J. of Organomet. Chem., 1989, 365, 61–73), from 1-methylimidazole (0.16 ml; 2 mmoles) and tributyltin chloride (0.56 ml; 2 mmoles). The stannyl derivative thus obtained is used directly for the following coupling reaction and is not isolated.

A solution of the preceding 2-(tributylstannyl)-1-methylimidazole (5 ml; 2 mmoles) in anhydrous THF is added, dropwise under argon, onto a suspension of dichlorobis(triphenylphosphine) palladium (II) (0.120 g;

0.17 mmoles) and 4-bromo-trifluoromethylbenzene (0.23 ml; 1.7 mmoles) in mxylene (4 ml). The reaction mixture is refluxed (≈120° C.), under argon, for 20 h. After having been washed with the aid of an aqueous solution of potassium fluoride, the reaction mixture is extracted 4 times with ethyl ether (v/v). The organic phases are combined, washed with a saturated sodium chloride solution, then dried over magnesium sulphate. After evaporation of the solvent under reduced pressure, the residual product is purified by chromatography on a silica column (eluent gradient: cyclohexane-ethyl acetate 30/70; then ethyl acetate 100; then ethyl acetate/methanol 95/5). The desired product is obtained as a beige solid (0.223 g).

Yield: 58%

Physical characteristics:

m.p.° C.: 115–116° C. (ethyl acetate);

NMR $^1$H: (CDCl$_3$); 3.79 ppm (s, 3H); 7.02 ppm (d, 1H; J=1.15 Hz); 7.16 ppm (d, 1H; J=1.15 Hz); 7.74 ppm (m symmetrical, 4H).

NMR $^{13}$C: (CDCl$_3$); 34.89 ppm (O); 123.68 ppm (O); 125.99 ppm (O); 126.03 ppm (E) (q, $^2J_{C-F}$=32 Hz); 128.02 ppm (O) (q, $^1J_{C-F}$=207 Hz); 129.28 ppm (O); 129.54 ppm (O); 130.65 ppm (E); 134.62 ppm (E).

MS: (EI, 70eV); 225 (M$^{+\cdot}$; 100); 156 (6); 145 (5); 113 (8); 84 (14); 49 (18).

B/ Preparation of bis-5-[2-[(4'-trifluoromethyl)phenyl]-5-seleno-1-methyl-imidazole]:

The desired product is obtained from the preceding derivative (0.198 g; 0.876 mmoles) and selenium I chloride (0.252 g; 1.1 moles) in anhydrous dichloromethane in following the same procedure as that described in Example 13/B. The desired product is obtained after purification by chromatography on a silica column (eluent gradient: ethyl acetate/cyclohexane 7/3, then pure ethyl acetate) as a yellow-orange solid (0.2123 g)

Yield: 79%

Physical characteristics:

m.p.° C.: 168–169° C. (ethyl acetate; partial sublimation);

NMR $^1$H: (CDCl$_3$); 3.71 ppm (s, 3H); 7.34 ppm (s, 1H); 7.72–7.83 ppm (m, 4H).

NMR $^{13}$C: (CDCl$_3$); 33.90 ppm (O); 118.81 ppm (E); 126.19 ppm (O); 126.22 ppm (E) (q, $^2J_{C-F}$=32 Hz); 127.9 ppm (O) (q, $^1J_{C-F}$=235 Hz); 129.56 ppm (O); 134.29 ppm (E); 140.26 ppm (O); 151.05 ppm (E).

NMR $^{77}$Se (CH$_3$SeCH$_3$); 401.6 ppm

MS: (EI, 70eV); 610 (M$^{30}$ $^{+\cdot}$; 8); 450 (12); 305 (100).

Example 18

Preparation of bis-5-[2-[(4'-carbomethoxy)phenyl]-5-seleno-1-methyl-imidazole]: BXT 51047

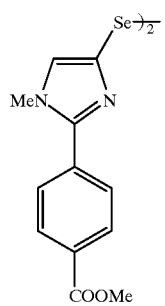

A/ Preparation of 2-[(4'-carbomethoxy)phenyl]-1-methyl-imidazole:

This derivative is obtained by a coupling reaction between 2-(tributylstannyl)-1-methylimidazole (whose preparation is identical to that used in Example 17/A) in solution in THF (5ml; 2.0 mmoles) and methyl 4-bromobenzoate (0.365 g; 1.7 mmoles) in the presence of dichlorobis (triphenylphosphine) palladium (II) (0.060 g; 0.085 mmoles) according to the same method as that described in Example 18/A. The desired product is purified by chromatography on a silica column (eluent gradient: cyclohexane-ethyl acetate 30/70; then ethyl acetate 100; then ethyl acetate/methanol 95/5). The desired product is obtained as a white solid (0.141g).

Yield: 40%

Physical characteristics:

m.p.° C.: 133–134° C. (ethyl acetate);

NMR $^1$H: (CDCl$_3$); 3.77 ppm (s, 3H); 3.92 ppm (s, 3H); 6.99 ppm (d, 1H, J=1.22 Hz); 7.14 ppm (d, 1H, J=1.22 Hz); 7.72 ppm (m symmetrical, 2H); 8.10 ppm (m symmetrical, 2H).

NMR $^{13}$C: (CDCl$_3$); 34.99 ppm(O); 52.55 ppm(O); 123.72 ppm(O); 128.95 ppm(O); 129.54 ppm(O); 130.32 ppm(O); 130.45 ppm(E); 135.4 ppm(E); 147.25 ppm(E); 167.32 ppm(E).

MS: (EI; 70eV); 216 (M$^{+\cdot}$; 100); 185(29); 157(22)

B/ Preparation of bis-5-[2-[(4'-carbomethoxy)phenyl]-5-seleno-1-methyl-imidazole]:

A solution of selenium I chloride (0.30 g; 1.3 mmoles) in anhydrous dichloromethane (2.6 ml) is added dropwise, at ambient temperature and with stirring, to a solution of the preceding compound (0.280 g; 1.3 mmoles) in the same solvent (2.6 ml). After 17 h of reaction, the yellowish mixture is neutralised with the aid of a saturated sodium hydrogen carbonate solution, then extracted with ethyl ether. The organic phases are combined, washed with a saturated sodium chloride solution, then dried over MgSO$_4$. After evaporation of the solvent under reduced pressure, the residual product is purified by chromatography on a silica column (eluent gradient: ethyl acetate/cyclohexane 80/20; then pure ethyl acetate).

The desired product is obtained as a bright yellow solid (0.204 g).

Yield: 70%

Physical characteristics:

m.p.° C.: 196.5° C. (ethyl acetate);

NMR $^1$H: (CDCl$_3$); 3.71 ppm (s, 3H); 3.96 ppm (s, 3H); 7.35 ppm (s, 1H); 7.75 ppm (m symmetrical, 2H); 8.15 ppm (m symmetrical, 2H).

NMR $^{13}$C: (CDCl$_3$); 33.99 ppm (O); 52.65 ppm (O); 118.82 ppm (E); 129.14 ppm (O); 130.46 ppm (O); 131.21 ppm (E); 135.0 ppm (E); 140.28 ppm (O); 151.47 ppm (E); 167.10 ppm (E).

NMR $^{77}$Se (D$_2$O); 402.3 ppm

MS: (CI; isobutane); 591 (MH$^+$; 9); 511 (M-Se, 4); 311 (100); 296 (MH$^+$/2. 45)

Example 19

Preparation of bis-5-[2-[(4'-carboxyl)-phenyl]-5-seleno-1-methyl-imidazole]: BXT 51046.

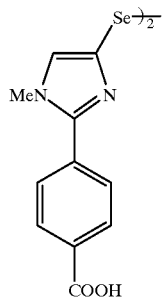

The derivative BXT 51047 (0.025 g; 0.05 mmoles), obtained in Example 18/B, is dissolved in 0.5 ml of a mixture methanol-water (3:1). Cooled to 5° C., an aqueous solution of lithium hydroxide in the same proportions as the two preceding solvents (0.030 g; 0.5 mmoles), is added to this suspension. After a 17-hour reaction, at this temperature, the yellow suspension obtained is treated according to method (3), already cited in Example 16. The residual product, taken up into a minimum of methanol, is purified by chromatography on a silica column (eluent gradient: methanol/ethyl acetate 40/60, then methanol/ethyl acetate 80/20). The desired product is obtained as a yellow solid (0.028 g).

Yield: 92%

Physical characteristics

NMR $^1$H: ($CD_3OD$); 3.76 ppm (s, 3H); 7.22 ppm (s, 1H); 7.67 ppm (m symmetrical, 2H); 8.11 ppm (m symmetrical, 2H)

NMR $^{13}$C: ($CD_3OD$); 34.25 ppm (O); 119.7 ppm (E); 129.82 ppm (O); 131.02 ppm (O); 132.95 ppm (E); 139.58 ppm (O); 140.85 ppm (E); 153.54 ppm (E); 174.79 ppm (E).

NMR $^{77}$Se ($D_2O$); 402.3 ppm

II/Activities:

The operatory protocols described below are non-limiting examples of applications of the method according to the invention.

Example 20

Measurement of the Glutathione Peroxidase Activity of Compounds of General Formula I The glutathione peroxidase activity is determined by using a 50 mM HEPES buffer, pH=7.3 (at 37° C.), containing 0.2 mM DTPA, 0.144 mM NADPH, 2.2 mM reduced glutathione (GSH) and 1.1 U/ml glutathione disulphide reductase. This buffer further contains 110 U/ml catalase when hydrogen peroxide is not used as substrate.

To 1.5 ml of the buffer described above, are added 100 μl of an ethanolic stock solution of the compound tested or 100 μl of absolute ethanol (blank). Each compound is tested at a final concentration of 10 μM. The reaction medium is equilibrated for 2 minutes at 37° C. Then 50 μl of 6.6 mM tert-butyl hydroperoxide (t-BuOOH) in ultrapure water, or 3.3 mM hydrogen peroxide ($H_2O_2$) in ultrapure water are added. The glutathione peroxidase activity is determined at 37° C. by measuring the decrease of absorbance at 340 nm for 5 minutes. Said activity or initial enzymatic rate is proportional to the slope of the variation of absorbance with time.

The catalytic activity of oxygen reduction of the compounds tested corresponds to the rate of consumption of NADPH in the absence of hydroperoxide. When this rate is significantly greater than that of the control, the corresponding glutathione oxidase activity can be checked by the direct measurement of the kinetics of consumption of the dissolved oxygen with the aid of a Clark electrode.

The results of the glutathione peroxidase activity measurements are shown in Table 1 below. They are expressed in nmoles of hydroperoxide reduced per minute.

TABLE 1

| Glutathione peroxidase activity (in nmoles of hydroperoxide reduced/min) pH = 7.3; 37° C.; [GSH] = 2 mM | | |
|---|---|---|
| | t-BuOOH | $H_2O_2$ |
| BXT-51079 | 7.9 | 13.9 |
| BXT-51099 | 9.6 | 31.1 |
| BXT-51104 | 16.8 | 44.7 |
| BXT-51108 | 24.7 | 46.8 |
| BXT-51110 | 14.3 | n.d. |
| BXT-51111 | 12.9 | n.d. |
| BXT-51125 | 17.7 | n.d. | n.d. = non-determined

As shown in Table 1 the compounds of general structure I described in the present invention catalyze, in the presence of glutathione GSH, the reduction of hydrogen peroxide or that of an organic hydroperoxide.

Example 21

Inhibition of the TNF-α-Induced Release of Interleukin 8 by Endothelial Cells

It is well known to the person skilled in the art that the release of interleukin 8 (IL8) causes a massive accumulation of activated neutrophils and thus participates in the inflammatory process and/or tissue degradation process (see Baggiolini M. et al.; FEBS Letters, 307, 1, 97–101, 1992).

Human endothelial cells are grown at 37° C. in multi-well plates under a water-saturated atmosphere constituted of a gaseous mixture of 95% air and 5% $CO_2$. Their culture medium is constituted by a medium M 199 pH=7.4 containing 20% foetal calf serum, 2 mM L-glutamine, 100 U/ml penicillin, 100 μg/ml streptomycin and 1% by volume of a medium supplement containing heparin and a growth factor for these cells.

When the cells are close to confluence, they are incubated for one hour in the presence or in the absence of one of the tested compounds of formula (I). This compound of the invention is incorporated at 5 μM in the culture medium containing 2% foetal calf serum, everything else being equal. After removal of the culture medium, the cells are incubated in the presence or in the absence (control) of TNF-α, at 1 ng/ml, in the same culture medium as before. In the case of cells pre-treated with a compound of the invention, the medium further contains the same compound at 5 μM. After three hours and thirty minutes of incubation, the interleukin 8 (IL-8) released into the culture medium is determined by ELISA.

The results obtained are given in the annexed FIG. 1. These results show that the incubation of the endothelial cells in the presence of TNF-α leads to an increase in the production of L-8 in the culture medium, and that the treatment of the cells by the compounds of formula (I) inhibits this effect by at least 70%.

These results demonstrate that such compounds can act as TNF-α antagonists in terms of interleukin 8 release by endothelial cells.

Example 22

Inhibition of TNF-α-Induced P- and E-selectin Expressions by Endothelial Cells It has been shown that the initial phase of inflammation is mediated by adhesion molecules of the E- and/or P-selectin type (see ALBELDA S. M. et al., FASEB Journal, 8, 504–512, 1994).

Human endothelial cells are grown under the same conditions as those described in Example 21.

When the cells are close to confluence, they are incubated for one hour in the presence or in the absence of one of the tested compounds of formula (I). This compound of the invention is incorporated at 5 μM in the culture medium containing 2% foetal calf serum, everything else being equal. After the removal of the culture medium, the cells are incubated in the presence or in the absence (control) of TNF-α, at 1 ng/ml, in the same culture medium as before. In the case of cells pre-treated with a compound, the medium further contains the same compound at 10 μM. After three hours and thirty minutes of incubation, the cells are washed with PBS buffer and they are fixed with 2% formaldehyde in the same buffer. The P- and E- selectin expressions on the cells are then measured by an ELISA determination by successively incubating the cells in the presence of a mouse monoclonal antibody, anti-P-selectin and anti-E-selectin respectively, and a rabbit anti-mouse anti-antibody labelled with alkaline phosphatase. The quantification is carried out upon the addition of para-nitrophenyl phosphate whose hydrolysis is followed at 405 nm.

The results obtained corresponding to the measurements of P- and E-selectin expressions are shown in the annexed FIGS. 2 and 3 respectively. These results show that the incubation of endothelial cells in the presence of TNF-α induces the expression of P- and E-selectin, which is inhibited by at least 75% and 90%, respectively, when the cells are treated with the tested compounds of formula (I).

The results show that such compounds are capable of inhibiting the TNF-α-induced expression of cell adhesion molecules such as P- and E-selectin.

The whole of these results show that the compounds of the invention having formula I:

1/ catalyse the reduction of hydroperoxides in the presence of glutathione;
2/ antagonize the action of TNF-α;
3/ inhibit the expression of cell adhesion molecules.

TNF-α, as well as the expression of adhesion molecules such as P- and E-selectins, having been implicated in pathologies caused by an over-production of hydroperoxides, the molecules of the present invention of the general formula I therefore constitute valuable active principles and, after formulation, powerful drugs enabling the treatment of the corresponding pathologies.

We claim:
1. Organoselenium compounds of general formula (I):

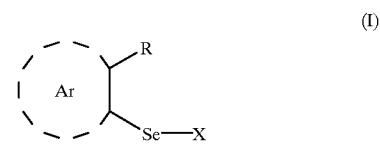

in which:

R=—C($R_1R_2$)—A—B;

$R_1$32 lower alkyl optionally substituted aryl; optionally substituted lower aralkyl;

$R_2$32 lower alkyl; optionally substituted aryl: optionally substituted lower aralkyl;

A=CO; $(CR_3R_4)_n$;

B represents $NR_5R_6$; $N^+R_5R_6R_7Y^-$; $OR_5$; $SR_5$;

Ar=an optionally substituted phenyl group

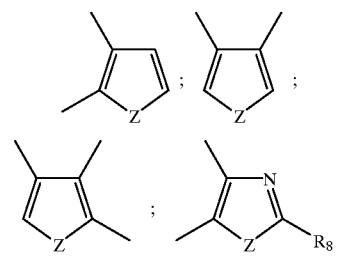

X=Ar(R)—Se—; —S-glutathione; —S-N-acetylcysteine; —S-cysteine; —S-penicillamine; —S-alburnin; —S-glucose;

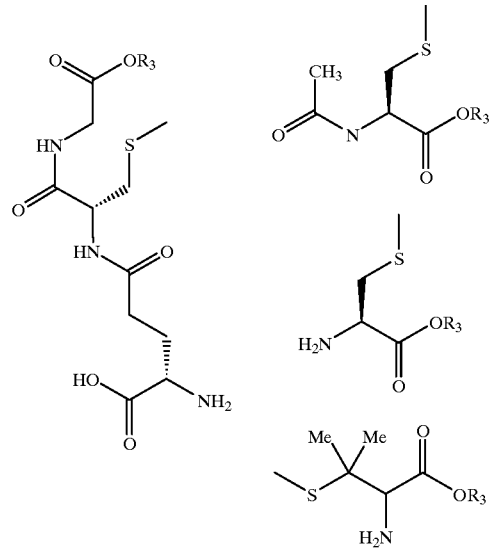

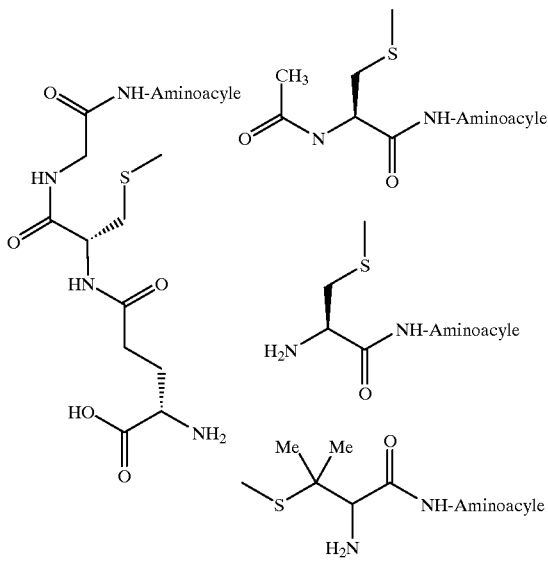

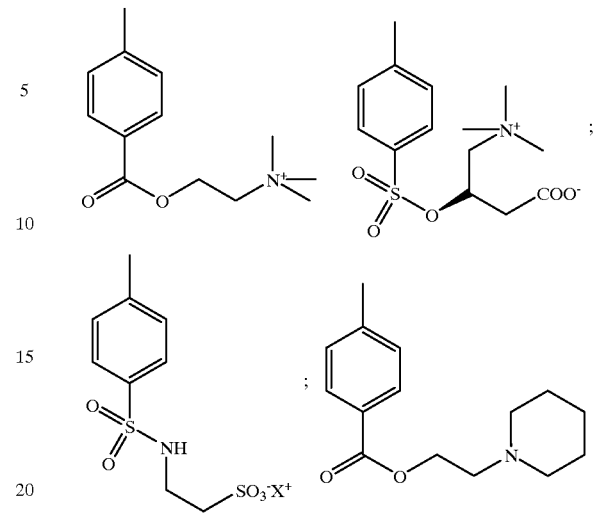

$R_3$=hydrogen; lower alkyl; optionally substituted aryl, optionally substituted lower aralkyl;

$R_4$=hydrogen; lower alkyl; optionally substituted aryl: optionally substituted lower aralkyl;

$R_5$=hydrogen; lower alkyl; optionally substituted aryl: optionally substituted lower aralkyl; optionally substituted heteroaryl; optionally substituted lower heteroaralkyl; CO(lower alkyl); CO(aryl); $SO_2$ (lower alkyl); $SO_2$(aryl);

$R_6$=hydrogen; lower alkyl; optionally substituted aryl; optionally substituted lower aralkyl; optionally substituted heteroaryl; optionally substituted lower heteroaralkyl;

$R_7$=hydrogen; lower alkyl; optionally substituted aryl: optionally substituted lower aralkyl; optionally substituted heteroaryl; optionally substituted lower heteroaralkyl;

$R_8$=hydrogen; lower alkyl; optionally substituted aryl; optionally substituted lower aralkyl; optionally substituted heteroaryl; optionally substituted lower heteroaralkyl; trifluoromethyl;

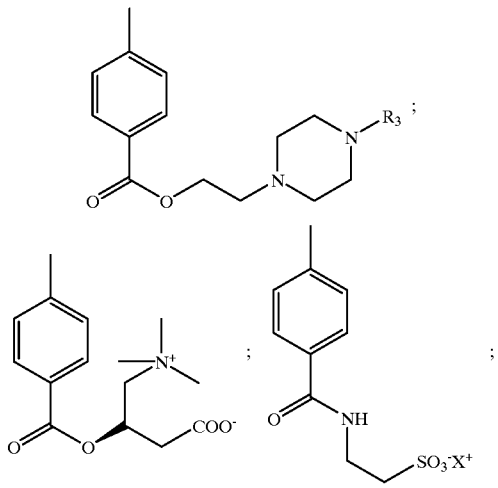

n=0 or 1;

$X^+$ represents the cation of a pharmaceutically acceptable base;

$Y^-$ represents the anion of a pharmaceutically acceptable acid;

and their salts of pharmaceutically acceptable acids or bases;

with the provisos that:
when R=—$C(R_1R_2)$—$(CR_3R_4)$—B with B=$NR_5R_6$ or $N^+R_5R_6R_7Y^-$ and
X=Ar(R)—Se— with Ar=optionally substituted phenyl,
then —$C(R_1R_2)$ is different from $(CR_3R_4)$; and
when Ar=phenyl and
R=—$C(R_1R_2)$—C(O)—B with B=$NH_2$ or $NHCH_3$ or $NHCH_2C_6H_5$ or $NHC_6H_5$ and
X=Ar(R)—Se—,
then $R_1$ and $R_2$ cannot simultaneously represent a methyl group.

2. Antioxidant compositions comprising an organoselenium compound of formula (I) of claim 1.

3. A method for storing a graft for transplantation of organs of human or animal origin by placing said graft in an adapted storage medium comprising the step of adding to said storage medium an effective amount of at least one compound of formula (I) of claim 1.

4. The method of claim 3 wherein said graft is selected from the group consisting of the heart, the liver, the kidney and the lungs.

5. A method of treatment of a patient suffering from functional impairments of cells or tissues related to an over-production of cytotoxic hydroperoxides, comprising administering to said patient an effective amount of at least one compound of formula (I) of claim 1.

6. The method of claim 5 wherein said patent is suffering from a pathology selected from the group consisting of
inflammatory cardiovascular pathologies; inflammatory cerebrovascular pathologies; ischemic cardiovascular pathologies; ischemic cerebrovascular pathologies;
inflammatory digestive pathologies; ischemic digestive pathologies;
inflammatory respiratory pathologies; ischemic respiratory pathologies;
inflammatory ophthalmic pathologies; ischemic ophthalmic pathologies;

cataracts;

acute ophthalmic allergies;

impairments of the retina which are associated with macular degeneration;

viral infections causing an immunodeficiency; and post-radiotherapy fibroses.

7. The method of claim 5 wherein said patient is suffering from a pathology selected from the group consisting of inflammatory diseases of the bowel;

adult respiratory distress syndrome; infant respiratory distress syndrome;

and AIDS.

8. The method of claim 7, wherein said pathology is Crohn's disease or hemorrhagic rectocolitis.

9. The method of claim 5 wherein the over-production of cytotoxic hydroperoxide is due to the activation of the intra-cellular metabolic pathways;

to the activation of enzymes contained in endothelial cells or in blood platelets;

to the activation by cytokines; to the activation of inflammatory or immune cells; to an intoxication by a free-radical generating xenobiotic;

to a voluntary irradiation, or to an accidental irradiation.

10. A pharmaceutical composition which comprises at least one organoselenium compound of formula (I) of claim 1, or one of its pharmaceutically acceptable salts of an acid or a base.

11. The pharmaceutical composition according to claim 10, wherein said organoselenium compound of formula (I) is present in an amount between 0.1 and 5% by weight based on the total weight of the composition.

12. The pharmaceutical composition according to claim 10, wherein it is in the form of a unit dose comprising from 1 to 500 mg.

13. Method of preparation of organoselenium compounds according to claim 1, of general formula (I), in which $R=-C(R_1R_2)-A-B$ ($R \neq H$); characterised in that it comprises the following essential steps:

a/ preparing or using an orthohalo arylacetonitrile derivative, optionally mono-or gem- disubstituted in the benzylic position; then, according to the series considered:

for the preparation of said compounds of formula (I) in which $A=(CR_3R_4)_m$ with n=0 (A does not exist):

b1/ hydrolyzing said nitrile derivative into an amide derivative, c1-1/ transforming this into an amine derivative by a transposition reaction according to conventional methods, d1-1/ allowing said amine derivative to react with a nucleophilic selenium derivative, optionally generated in situ, in the presence of a copper Cu(I) salt, in a polar organic solvent, to lead to the corresponding arylisoselenazoline derivative, e1-1/ optionally, N-alkylating or N-arylating or N-acylating or N-sulphonylating, according to conventional procedures, said aryliso-selenazoline derivative;

for the preparation of said compounds of formula (I) in which A=CO:

b1/ hydrolyzing said nitrile derivative into an amide derivative, c1-2/ allowing said amide derivative to react with a nucleophilic selenium derivative, optionally generated in situ, in the presence of a copper Cu(I) salt, in a polar organic solvent, to lead to the corresponding aryliso-selenazone derivative, d1-2/ optionally, N-alkylating or N-arylating or N-acylating or N-sulphonylating, said arylisoselenazone derivative;

for the preparation of said compounds of formula (I) in which $A=CH_2$:

b2/ reducing said nitrile derivative into an amine derivative, with the aid of borane for example in an ethereal solvent such as tetrahydrofuran for example, c2/ allowing said amine derivative to react with a nucleophilic selenium derivative, optionally generated in situ, in the presence of a copper Cu(I) salt, in a polar organic solvent, to lead to the corresponding aryliso-selenazine derivative, d2/ optionally, N-alkylating or N-arylating or N-acylating or N-sulphonylating, according to conventional procedures, said aryliso-selenazine derivative;

for the preparation of said compounds of formula (I) in which $A=(CR_3R_4)$ ($\neq CH_2$):

b3/ carrying out a mono- or a bis-C-alkylation of said nitrile derivative according to conventional methods, with the aid of an organolithium derivative for example in an ethereal solvent such as tetrahydrofuran;

c3/ allowing the amine derivative obtained to react with a nucleophilic selenium derivative, optionally generated in situ, in the presence of a copper Cu(I) salt, in a polar organic solvent, to lead to the corresponding arylisoselenazine derivative;

d3/ optionally, N-alkylating or N-arylating or N-acylating or N-sulphonylating, according to conventional procedures, said corresponding arylisoselenazine derivative;

b/ reducing, in a polar solvent such as methanol, the cyclic compound obtained, according to any one of the above synthetic routes, with the aid of a metal hydride, such as sodium borohydride, intervening in an amount corresponding to a half-reducing equivalent; for the preparation of said compounds of formula (I) in which $X=Ar(R)-Se-$; or allowing said cyclic compound obtained according to any one of the above synthetic routes to react at ambient temperature, with the thiol compound corresponding to the values of $X \neq Ar(R)-Se-$, for the preparation of said compounds of formula (I) in which $X \neq Ar(R)-Se-$.

14. An organoselenium compound of general formula (I), according to claim 1, selected from the group consisting of di[2-[2'-(1'-amino-2'-methyl)propyl]phenyl]-diselenide; di[2-[2'-(1'-amino-2'-methyl)propyl]phenyl]-diselenide dihydrochloride; di[2-[2'-(1'-ammonium-2'-methyl)propyl]phenyl]-diselenide di-paratoluenesulphonate; di[2-[2'-(1'-amino-2'-methyl)propyl]-4-methoxy]phenyl-diselenide; di[2-[2'-(1'-methylamino-2'-methyl)propyl]phenyl]-diselenide; di[2-[2'-(1'-methylamino-2'-methyl)propyl phenyl]-diselenide dihydrochloride; di[2-[2'-( 1 '-dimethylamino-2'-methyl)propyl]phenyl]-diselenide; di[2-[2'-(1'-trimethylammonium-2'-methyl)propyl]phenyl]-diselenide di-paratoluenesulphonate; S-(N-acetyl-L-cysteinyl)-[2-[2'-(1'-amino-2'-methyl)-propyl]phenyl]-selenide; and S-glutathionyl-[2-[2'-(1'-amino-2'-methyl)-propyl]-phenyl]-selenide.

* * * * *

UNITED STATES PATENT AND TRADEMARK OFFICE
CERTIFICATE OF CORRECTION

PATENT NO : 5,973,009
DATED : October 26, 1999
INVENTOR(S) : Catherine Tailhan-Lomont et al.

It is certified that error appears in the above-identified patent and that said Letters Patent is hereby corrected as shown below:

Please delete claim 1 in its entirety and replace herewith:

--1. Organoselenium compounds of general formula (I):

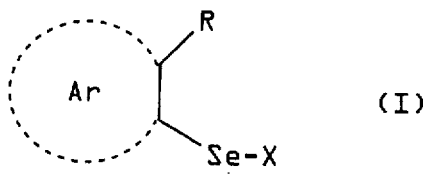

in which:

$R = -C(R_1R_2)-A-B$;

$R_1$ = lower alkyl; optionally substituted aryl; optionally substituted lower aralkyl;

$R_2$ = lower alkyl: optionally substituted aryl: optionally substituted lower aralkyl;

$A = CO$; $(CR_3R_4)_n$;

B represents $NR_5R_6$ ; $N^+R_5R_6R_7Y^-$; $OR_5$; $SR_5$;

UNITED STATES PATENT AND TRADEMARK OFFICE
CERTIFICATE OF CORRECTION

PATENT NO : 5,973,009
DATED : October 26, 1999
INVENTOR(S) : Catherine Tailhan-Lomont et al.

It is certified that error appears in the above-identified patent and that said Letters Patent is hereby corrected as shown below:

$R_3$ = hydrogen; lower alkyl; optionally substituted aryl; optionally substituted lower aralkyl;

$R_4$ = hydrogen; lower alkyl; optionally substituted aryl; optionally substituted lower aralkyl;

$R_5$ = hydrogen; lower alkyl; optionally substituted aryl; optionally substituted lower aralkyl; optionally substituted heteroaryl; optionally substituted lower heteroaralkyl; CO(lower alkyl); CO(aryl); $SO_2$ (lower alkyl); $SO_2$(aryl);

$R_6$ = hydrogen; lower alkyl; optionally substituted aryl; optionally substituted lower aralkyl; optionally substituted heteroaryl; optionally substituted lower heteroaralkyl;

$R_7$ = hydrogen; lower alkyl; optionally substituted aryl: optionally substituted lower aralkyl; optionally substituted heteroaryl; optionally substituted lower heteroaralkyl;

n = 0 or 1;

UNITED STATES PATENT AND TRADEMARK OFFICE
CERTIFICATE OF CORRECTION

PATENT NO : 5,973,009
DATED : October 26, 1999
INVENTOR(S) : Catherine Tailhan-Lomont et al.

It is certified that error appears in the above-identified patent and that said Letters Patent is hereby corrected as shown below:

Ar = an optionally substituted phenyl group;

X = Ar(R)-Se-; -S-glutathione; -S-N-acetylcysteine; -S-cysteine; -S-penicillamine; -S-albumin; -S-glucose;

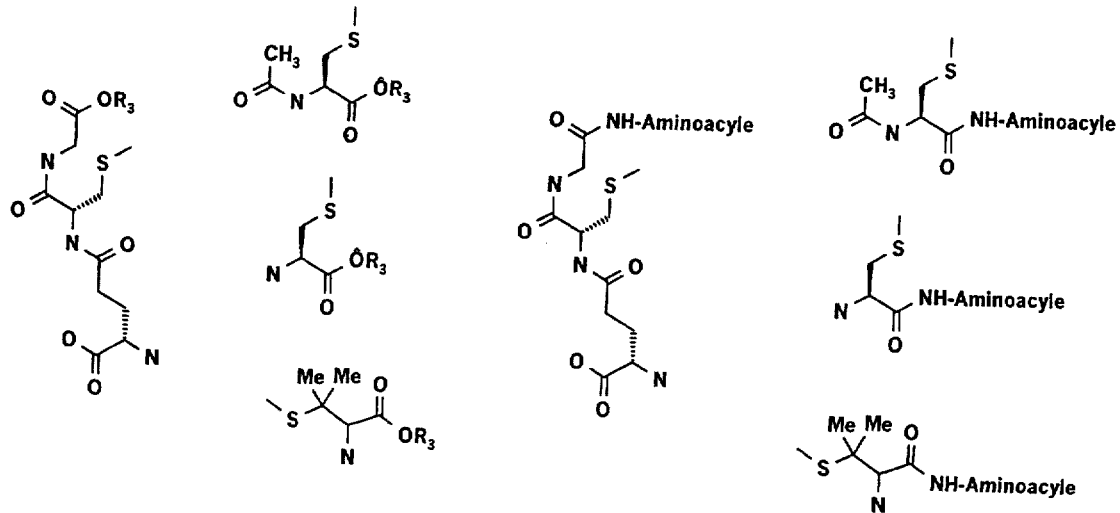

UNITED STATES PATENT AND TRADEMARK OFFICE
CERTIFICATE OF CORRECTION

PATENT NO : 5,973,009
DATED : October 26, 1999
INVENTOR(S): Catherine Tailhan-Lomont et al.

It is certified that error appears in the above-identified patent and that said Letters Patent is hereby corrected as shown below:

$Y^-$ represents the anion of a pharmaceutically acceptable acid;

and their salts of pharmaceutically acceptable acids or bases;

with the provisos that:

when $R = -C(R_1R_2)-(CR_3R_4)-B$ with $B = NR_5R_6$ or $N^+R_5R_6R_7Y^-$ and $X = Ar(R)-Se-$ with $Ar$ = optionally substituted phenyl, then $-C(R_1R_2)$ is different from $(CR_3R_4)$; and when $Ar$ = phenyl and $R = -C(R_1R_2)-C(O)-B$ with $B=NH_2$ or $NHCH_3$ or $NHCH_2C_6H_5$ or $NHC_6H_5$ and $X = Ar(R)-Se-$, then $R_1$ and $R_2$ cannot simultaneously represent a methyl group. --

UNITED STATES PATENT AND TRADEMARK OFFICE
CERTIFICATE OF CORRECTION

PATENT NO : 5,973,009
DATED : October 26, 1999
INVENTOR(S) : Catherine Tailhan-Lomont et al.

It is certified that error appears in the above-identified patent and that said Letters Patent is hereby corrected as shown below:

Column 5, line 25, change "32" to -- = --.

Column 5, line 27, change "32" to -- = --.

Column 5, line 35, change "32" to -- = --.

Column 5, line 39, change "32" to -- = --.

Column 5, line 43, change "32" to -- = --.

Signed and Sealed this

Fifteenth Day of August, 2000

Attest:

Q. TODD DICKINSON

*Attesting Officer*  *Director of Patents and Trademarks*